(12) United States Patent
Valsan et al.

(10) Patent No.: US 7,276,627 B2
(45) Date of Patent: Oct. 2, 2007

(54) ONE POT SEQUENTIAL REACTIONS AND NOVEL PRODUCTS PRODUCED THEREBY

(75) Inventors: Nandakumar Mecheril Valsan, Ames, IA (US); John G. Verkade, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 140 days.

(21) Appl. No.: 11/099,415

(22) Filed: Apr. 5, 2005

(65) Prior Publication Data

US 2006/0224017 A1    Oct. 5, 2006

(51) Int. Cl.
C07C 303/00    (2006.01)
(52) U.S. Cl. .................................................... 562/872
(58) Field of Classification Search ................. 564/13, 564/395, 431; 562/872
See application file for complete search history.

(56) References Cited

U.S. PATENT DOCUMENTS 4,014,870 A * 3/1977 Meyer ........................ 548/224

FOREIGN PATENT DOCUMENTS

| DE | 331543 | 11/1983 |
|----|--------|---------|
| DE | 3342724 | 5/1984 |
| EP | 144791 A2 | 6/1985 |

OTHER PUBLICATIONS

Sigma-Aldrich Catalogue, Missouri 1993 p. 918.*
Loones, K.T.J. et al. The first tandem double palladium-catalyzed aminations:synthesis of dipyrido[1,2-a:3',2'-d]imidazole and its benzo- and aza-analogues. Chem.Commun, (2004) 2466-2467.*
Marion, n. et al. Synthesis of Biaryl, Arylamine and Aryk Ketone Compounds Using a Commercially Available Air- and Moisture-Stable Palladium Catalyst. SYNTHESIS (2003) No. 16, 2590-2592.*
Behl, M., et al., "Tailored Semiconducting Polymers: Living Radical Polymerization and NLO-Functionalization of Triphenylamines", Macromolecular Chemistry and Physics, 203(3), (2002), 503-510.
Cao, X.-D., et al., "Synthesis and Photoconductive Properties of N, N-Bis (4-methylphenyl)—4-[2-(4-methylphenyl) ethenyl] benzenamine", Jingxi Huagong = Fine Chemicals, (2003), 452-454.
Collot, V., et al., "First Combined Selective N- and C-arylations With Boronic Acids: Application to the Synthesis of 1,3-diarylindazoles", Tetrahedron Letters, 41(47), (Nov. 18, 2000), 9053-9057.
Cuny, G., et al., "One-Pot Synthesis of Polyheterocycles by a Palladium- Catalyzed Intramolecular N-Arylation/C-H Activation/Aryl-Aryl Bond-Forming Domino Process.", Angewandte Chemie International Edition, 42(39), (Oct. 13, 2003), 4774-4777.

Edmondson, S. D., et al., "Palladium-Catalyzed Coupling of Vinylogous Amides with Aryl Halides: Applications to the Synthesis of Heterocycles", Organic Letters, 2(8), (Apr. 20, 2000), 1109-1112.
Fujimaki, Y., et al., "Near-Infrared sensitive electrophotographic photoconductors using oxotitanium phthalocyanine", Journal of Imaging Technology, 17(5), (Oct./Nov. 1991),202-206.
Gajare, A. S., et al., "Application of a Diphosphinidenecyclobutene Ligand in the Solvent-Free Copper-Catalysed Amination Reactions of Aryl Halides", Chemical Communications, 2004(17), (2004),1994-1995.
Hartwig, J. F., "Carbon-Heteroatom Bond-Forming Reductive Eliminations of Amines, Ethers, and Sulfides", Accounts of Chemical Research, 31(12), (Dec. 1998),852-860.
Hartwig, J. F., "Transition Metal Catalyzed Synthesis of Arylamines and Aryl Ethers from Aryl Halides and Triflates: Scope and Mechanism", Angewandte Chemie International Edition, 37(15), (Aug. 17, 1998), 2046-2067.
Khedkar, V., et al., "Efficient One-Pot Synthesis of Tryptamines and Tryptamine Homologues by Amination of Chloroalkynes", Tetrahedron Letters, 45(15), (Apr. 5, 2004), 3123-3126.
Lee, H. J., et al., "Triphenylamine-Cored Bifunctional Organic Molecules for Two-Photon Absorption and Photorefraction", Chemistry of Materials, 16(3), (2004), 456-465.
Lin, T.-C., et al., "Degenerate Nonlinear Absorption and Optical Power Limiting Properties of Asymmetrically Substituted Stilbenoid Chromophores", Journal of Materials Chemistry, 14(6), (2004), 982-991.
Matyus, P., et al., "New Pathways Towards Pyridazino-Fused Ring Systems", Synlett, 7. (Jun. 2004), 1123-1139.
Muci, A. R., et al., "Practical Palladium Catalysts for C-N and C-O Bond Formation", Topics in Current Chemistry, vol. 219, (2002), 131-209.
Negishi, E.-I. , et al., "Table of Contents and Preface", Handbook of Organopalldium Chemistry for Organic Synthesis, Wiley-Interscience, New York, NY,(2002), 11 pgs.
Oda, Y., et al., "Near-Infrared Sensitive Photoreceptors Incorporating a New Polymorph of Oxotitanium Phthalocyanine", Denshi Shashin Gakkaishi = Electrophotography, 29, (1990), 250-258.
Sengupta, S., et al., "A Tetraphenylmethane Based Starbust Triarylamine Cluster: Spectroscopy, Electrochemistry and Morphological Studies", Tetrahedron Letters, 43(19), (May 6, 2002), 3521-3524.

(Continued)

Primary Examiner—Johann Richter
Assistant Examiner—M Louisa Lao
(74) Attorney, Agent, or Firm—Schwegman, Lundberg, & Woessner P.A.

(57) ABSTRACT

A method for producing sequenced reaction products comprising performing, in one pot, a first reaction at a lower temperature followed by a second reaction at a higher temperature in the presence of a catalyst system comprising a proazaphosphatrane in combination with a palladium compound is provided. In one embodiment, the first reaction is a double amination reaction and the second reaction is an arylation. Use of one pot and a single catalyst system for each set of sequential reactions is efficient and economical. Novel N,N-diarylaminostyrenes and N,N-diarylaminostilbenes are produced according to the methods described herein.

21 Claims, No Drawings

OTHER PUBLICATIONS

Siebeneicher, H., et al., "A Flexible and Catalytic One-Pot Procedure for the Synthesis of Indoles.", *Angewandte Chemie International Edition*, 42(26), (Jul. 7, 2003), 3042-3044.

Su, W., et al., "Highly Active Palladium Catalysts Supported by Bulky Proazaphosphatrane Ligands for Stille Cross-Coupling: Coupling of Aryl and Vinyl Chlorides, Room Temperature Coupling of Aryl Bromides, Coupling of Aryl Triflates, and Synthesis of Sterically Hindered Biaryls", *Journal of the American Chemical Society*, 126(50), (Dec. 22, 2004), 16433-16439.

Su, W., et al., "$Pd_2(dba)_3$/P(i-BuNCH$_2$CH$_2$)$_3$N-Catalyzed Stille Cross-Coupling of Aryl Chlorides", *Organic Letters*, 6(9), (Apr. 29, 2004), 1421-1424.

Thelakkat, M., "Star-Shaped, Dendrimeric and Polymeric Triarylamines as Photoconductors and Hole Transport Materials for Electro-Optical Applications", *Macromolecules Materials and Engineering*, 287(7), (2002), 442-461.

Tsuji, J., "Table of Contents, Preface and Abbreviations", *Palladium Reagents and Catalysis: Innovations in Organic Synthesis*, John Wiley & Sons, Chichester, England, (1995), 7 pgs.

Urgaonkar, S., et al., "P(i-BuNCH$_2$2CH$_2$)$_3$N: An Effective Ligand in the Palladium-Catalyzed Amination of Aryl Bromides and Iodides.", *Journal of Organic Chemistry*, 68(2), (Jan. 24, 2003), 452-459.

Urgaonkar, S., et al., "P[N(i-Bu)CH$_2$CH$_2$]$_3$N: A Versatile Ligand for the Pd-Catalyzed Amination of Aryl Chlorides ", *Organic Letters*, 5(6), (Mar. 20, 2003),815-818.

Urgaonkar, S., et al., "Pd/P(i-BuNCH$_2$CH$_2$)$_3$N: An Efficient Catalyst for Suzuki Cross-Coupling of Aryl Bromides and Chlorides with Arylboronic Acids", *Tetrahedron Letters*, 43(49), (Dec. 2, 2002), 8921-8924.

Verkade, J. G., "P(RNCH$_2$CH$_2$)$_3$N: Very Strong Non-Ionic Bases Useful in Organic Synthesis", *Topics in Current Chemistry*, vol. 223, (2002), 1-44.

Verkade, J. G., et al., "Proazaphosphatranes: a Synthesis Methodology Trip From Their Discovery to Vitamin A", *Tetrahedron*, 59(40), (Sep. 29, 2003), 7819-7858.

Verkade, J G., et al., "Recent Applications of Proazaphosphatranes in Organic Synthesis", *Aldrichimica Acta*, 37(1), (2004), 3-14.

Waring, D. R., et al., "Preface and Table of Contents", *The Chemistry and Application of Dyes*, Plenum Press, New York, (1990), 7 pgs.

Wolfe, J. P., et al., "Rational Development of Practical Catalysts for Aromatic Carbon-Nitrogen Bond Formation", *Accounts of Chemical Research*, 31(12), (Dec. 1998), 805-818.

Yamazaki, K. , et al., "Palladium-Catalyzed tandem *C,N*-arylation of Immobilized Enamine for Solid Phase Indole Synthesis", *Journal of the Chemical Society, Perkin Transactions 1*, 19, (2002), 2137-2138.

Yang, J S., et al., "Fluorescence Enhancement of *trans*4-Aminostilbene by N-Phenyl Substitutions: The "Amino Conjugation Effect"", *Journal of the American Chemical Society*124(11), (Mar. 20, 2002), 2518-27.

Yang, J S., et al., "Palladium-Catalyzed Synthesis of *trans*-4-(*N,N*-Bis(2-pyridyl)amino)stilbene. A New Intrinsic Fluoroionophore for Transition Metal Ions", *Organic Letters*4(5), (Mar. 7, 2002), 777-80.

Yang, J S., et al., "Spectroscopic Correlations Between Supermolecules and Molecules. Anatomy of the Ion-Modulated Electronic Properties of the Nitrogen Donor in Monoazacrown-Derived Intrinsic Fluoroionophores.", *Journal of Organic Chemistry*, 69(3), (Feb. 6, 2004), 719-726.

Yang, J S., et al., "Substituent-Dependent Photoinduced Intramolecular Charge Transfer in *N*-Aryl-Substituted *trans*-4-Aminostilbenes.", *Journal of the American Chemical Society*, 126(39), Oct. 6, 2004), 12325-12335.

Yang, J S., et al., "Zn(II)-Induced Ground-State pi-Deconjugation and Excited-State Electron Transfer in *N,N*-bis(2-pyridyl)amino-Substituted Arenes", *Journal of Organic Chemistry*, 69(10), (May 14, 2004), 3517-3525.

\* cited by examiner

ONE POT SEQUENTIAL REACTIONS AND NOVEL PRODUCTS PRODUCED THEREBY

STATEMENT OF GOVERNMENT RIGHTS

This invention was made with support of the United States Government under United States Department of Agriculture Natural Resources Conservation Service Contract No. 68-3A75-3-146. The Government has certain rights in this invention.

FIELD

The present invention relates to sequential reactions, and in particular, the present invention relates to one pot sequential reactions and novel products produced thereby.

BACKGROUND

Sequenced reactions are used to produce complex molecules, such as those in which both the C—N and C—C bonded moieties are fundamental features. Examples of such complex molecules include, but are not limited to 6-phenanthridinones and their heterocyclic analogs.

Examples of sequenced reactions used to form such products include, but are not limited to, transition metal-catalyzed sequential C—C and C-heteroatom bond forming reactions. This includes amination/intramolecular cyclization reaction sequences for the synthesis of indole derivatives such as 1,3-diphenylindazole; 1,3-di-p-tolylindazole; and 1-phenyl-3-p-methoxy phenyl indazole, and so forth. However, such sequenced reactions are costly and time-consuming as they require multiple catalysts (or catalyst systems) and/or multiple pots. These methods are also not necessarily environmentally friendly as there are typically large amounts of waste products generated.

Other complex molecules produced with sequenced reactions include N,N-diarylaminostilbenes. Known synthetic routes for these compounds begin from aniline and the corresponding aryl halides via a three step process involving an Ullmann, Vilsmeier and Wittig reaction sequence. Alternatively, these reactions can begin with triphenylamine as a starting material via a Vilsmeier, Wittig and palladium-catalyzed arylation reaction series. It is also possible to synthesize trans-4-N,N-diarylaminostilbenes from the corresponding halostilbenes or aminostilbenes using palladium catalyzed amination/arylation reactions. All such methods, however, require multiple catalysts (or catalyst systems) and/or more than one pot.

Thus, what is needed is an efficient and economical way to produce complex molecules, such as those in which both the C—N and C—C bonded moieties are fundamental features.

SUMMARY

A novel one pot, single catalyst system methodology for the sequential synthesis of complex molecules in which both the C—N and C—C bonded moieties are fundamental features is provided. Embodiments of the present invention provide for one pot reactions which comprise one or more aminations of one or more aryl halide reagents and an arylation to produce an intermediate product and an end product or products. It is also possible that pseudohalide reagents (e.g., triflates) could be used. The aminations are generally performed at a first temperature and the arylation is performed at a second, higher temperature. By varying the type and location of the aryl groups on an amino styrene core the stoichiometry of the final product can be controlled.

In one embodiment, two single aminations are performed at a first temperature followed by an arylation reaction at a second, higher temperature with a single aryl halide reagent to produce a combination of intermediate styrene products and stilbene end products. (See Scheme 1). In another embodiment, two single aminations are performed at a first temperature with a first aryl halide reagent to produce an intermediate styrene product which is reacted with a second aryl halide reagent at a second, higher temperature to produce a stilbene end product. In other embodiments, the double amination is performed with two different aryl halides. (See Schemes 2 and 3). In some embodiments, the end products are symmetrically substituted diarylaminostilbenes. In other embodiments, the end products are unsymmetrically substituted diarylaminostilbenes. In some embodiments, the intermediate diarylaminostyrene products (symmetrical and unsymmetrical) are novel.

In one embodiment, the invention comprises novel one pot methodologies for the synthesis of N,N-diarylaminostilbenes. In a particular embodiment, the invention comprises novel one pot methodologies for the synthesis of trans-4-N,N-diarylamino stilbenes. Synthesis of such molecules has previously required time-consuming, expensive multistep reactions which take place in more than one pot and/or use more than one catalyst or catalyst system. Embodiments of the invention have the additional advantage of being able to use the same catalyst system for each set of sequential reactions taking place in one pot, thus reducing costs and further increasing efficiency.

In one embodiment, a method for producing sequenced reaction products comprising performing, in one pot, a first reaction at a lower temperature followed by a second reaction at a higher temperature in the presence of a catalyst system comprising a proazaphosphatrane in combination with a palladium compound is provided.

In one embodiment, a method for producing a N,N-diarylaminostilbene comprising combining a styrene, one or more aryl halides, a homogenous catalyst of formula:

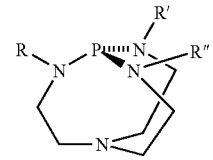

wherein R', R" and R'" are selected from the group consisting of H, $(C_1-C_8)$alkyl and $(C_6-C_9)$aryl under conditions wherein the homogenous catalyst, in combination with a palladium compound, form a catalyst system which catalyzes formation of the N,N-diarylaminostilbene is provided.

Novel intermediates have also been produced using conventional amination reactions. In one embodiment, novel N,N-diarylaminostyrenes have been produced.

Yields are at least comparable or higher as compared with known multi-pot methods. In one embodiment total yields are between about 41 and 98%. In a particular embodiment, total yields are between about 80 and 98%.

In a particular embodiment, syntheses of trans-4-N,N-diarylaminostilbenes having different substituents on the phenyl rings are accomplished from commercially available starting materials with a one pot sequential amination, such as two Buchwald-Hartwig aminations, followed by an intermolecular Heck reaction in the presence of a Pd$_2$(dba)$_3$/P(i-BuNCH$_2$CH$_2$)$_3$N catalyst system. In one embodiment, the catalyst loading is no greater than known mono-amination reactions, such as about 2 mol % of Pd$_2$(dba)$_3$ and 4 mol % of a superbase catalyst.

By using the same catalyst system for each sequenced reaction, the synthesis can be performed in a single pot without the need for a second catalyst system. As a result selective coupling of a C—C and C—N bond of various compounds (e.g., styrenyl compounds) can now be achieved in a one pot reaction by sequential addition of a reagent (e.g., aryl halide) under conditions wherein the catalyst system catalyzes formation of the various compounds. By reducing the number of pots needed to perform such transformations as well as using only a single catalyst system, the process can now be performed more economically and in a more environmentally-friendly way. The methods described herein are also generally faster than known methods for synthesizing these compounds since known multi-pot methods require isolation, and sometimes purification, of each compound as it is produced.

The invention further comprises novel stilbene compounds produced according to the methods described herein. Such products may take on a number of configurations, but can generally be described as:

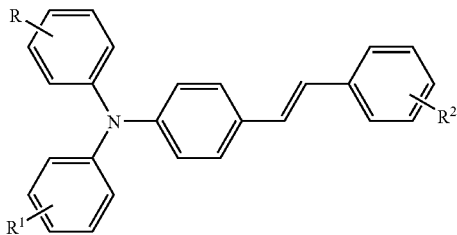

wherein R, R$^1$ and R$^2$=3,5-dimethyl, 3-CH$_3$, 3-CH$_3$-4-OCH$_3$ or 3-OCH$_3$; or R=R$^1$=3-OCH$_3$ and R$^2$=H; or R=R$_1$=4-OCH$_3$ and R$^2$=3-CH$_3$.

Novel intermediate products, i.e., N,N-diarylaminostyrenes have also been produced herein. Such products may take on a number of configurations, but can generally be described as:

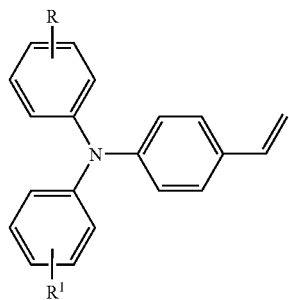

wherein R=R$^1$=3,5-dimethyl, 3-CH$_3$, 3-CH$_3$-4-OCH$_3$, 4-tert-butyl or 4-Cl, or R$^1$=4-CH$_3$ and R=4-OCH$_3$ or 3CH$_3$, or R$^1$=3-OCH$_3$ and R=4CH$_3$. Such products are useful in additional reactions performed in the same pot to produce various N,N-diarylaminostilbenes.

The end products discussed herein, i.e., the N,N-diarylaminostilbenes, can be used as dopants to make polymers potentially having photoconducting properties. These products can also be used as electrophotographic photoconductors and photoreceptors. Many of the compounds are also known to exhibit an amino conjugation effect in their fluorescence enhancement spectra. Other possible uses include use as a new ionophore for transition metals among several other applications. It is likely that many, if not all, of the novel compounds produced according to the novel methods described herein have the same or similar properties.

DETAILED DESCRIPTION OF THE EMBODIMENTS

Various one pot methods are described herein which allow sequential reactions to be performed producing, in some embodiments, novel compounds, including novel intermediates. Unlike known sequenced reactions, the same catalyst system can be used in each set of one pot sequential reactions. Total yields of up to 98% have been observed, although it is possible even higher yields can be obtained under other reaction conditions.

The description which follows contains a short definition section followed by a discussion of the various embodiments. Specific examples are also provided followed by a brief conclusion.

Definitions

The term "Heck Reaction" as used herein refers to a palladium-catalyzed C—C coupling between aryl halides and activated alkenes in the presence of a base. One of the benefits of the Heck Reaction is its outstanding trans selectivity. A Heck reaction can be intramolecular or intermolecular as is known in the art, but is limited herein to an intermolecular reaction. The intermolecular reaction can generally be described as follows:

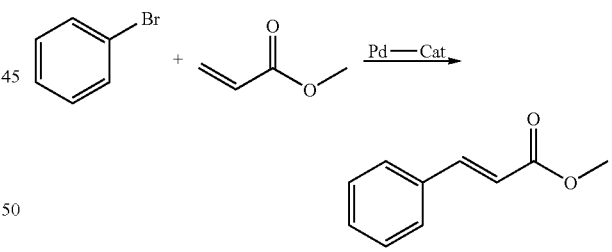

The general mechanism of the Heck reaction is known in the art. See also, J. Masllorens, M. Moreno-Manas, A. Pla-Quintana, A. Roglans, Org. Lett., 2003, 5, 1559-1561 and G. Battistuzzi, S. Cacchi, G. Fabrizi, Org. Lett., 2003, 5, 777-780.

The term "amination" as used herein refers to amination of an aryl halide or pseudohalide reagent. An amination reaction can be a single or double (bis) amination. Depending on the starting materials, reaction conditions, etc., the resulting amine can be a secondary or tertiary amine, or mixtures thereof. One type of amination reaction is a Buchwald-Hartwig Cross Coupling Reaction (hereinafter "Buchwald-Hartwig" reaction") which can be described generally as follows:

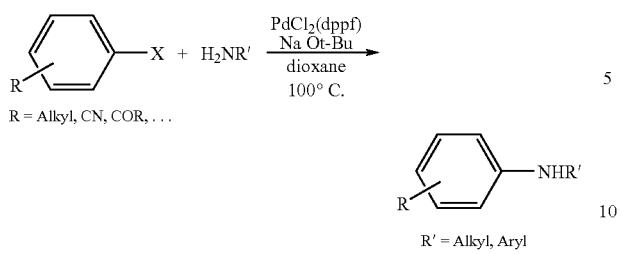

R = Alkyl, CN, COR, ...

R' = Alkyl, Aryl

A Buchwald-Hartwig reaction involves the synthesis of aryl amines utilizing palladium catalysts. Starting materials include aryl halides, pseudohalides (for example triflates) and primary or secondary amines. The general mechanism of the Buchwald-Hartwig reaction is known in the art. See also, D. Zim, S. L. Buchwald, *Org. Lett.*, 2003, 5, 2413-2415 and S. Urgaonkar, M. Nagarajan, J. G. Verkade, *J. Org. Chem.*, 2003, 68, 452-459.

The term "analog" as used herein refers to a compound that results from substitution, replacement, or deletion of various organic or inorganic groups and/or hydrogen atoms from a parent compound.

Discussion

Complex molecules having C—N and C—C bonded moieties can now be produced efficiently and economically using various embodiments of the present invention and in yields comparable to or better than yields obtained using known methodologies. Examples of such complex molecules include, but are not limited to, N,N-diarylaminostilbenes and their analogs, which are versatile compounds having application in the field of photochemistry. For example, these compounds can be used as dopants to make polymers having photoconducting properties. These products can also be used as electrophotographic photoconductors and photoreceptors. Many of the compounds are also known to exhibit an amino conjugation effect in their fluorescence enhancement spectra. Other possible uses include use as a new ionophore for transition metals among several other applications. See, for example, Patent App. Serial No. DE 83-3315437 19830428 to M. Sasaki, (1983); Y. Oda, T. et al., *Denshi Shashin Gakkaishi* 1990, 29, 250-258; Y. Fujimaki, et al, *Journal of Imaging Technology*, 1991, 17, 202-206; J. S. Yang, et al, *J. Am. Chem. Soc.* 2003, 124, 2518-2527; J. S. Yang, et al, *Org. Lett.* 2002, 4, 777-780; J. S. Yang, et al., *J. Org. Chem.* 2004, 69, 719-726; J. S. Yang, et al, *J. Org. Chem.* 2004, 69, 3517-3525; and J. S. Yang, et al., *J. Am. Chem. Soc.* 2003, 124, 12325-12335. It is likely that many, if not all, of the novel compounds produced according to the novel methods described herein have the same or similar properties.

Catalyst systems useful herein include proazaphosphatranes, in combination with palladium, such as $Pd_2(dba)_3$, i.e., tris(dibenzylideneacetone)dipalladium(0). In other embodiments, it may be possible to use other palladium compounds such as palladium salts (e.g., $Pd(OAc)_2$) or Pd(0) powder. It is also possible that copper, instead of the palladium compound, may be useful herein since it is known to be useful in aminations, although its usefulness with arylation reactions has not yet been established. Proazaphosphatranes are described in U.S. Pat. Nos. 5,260,436 and 5,051,533, both of which are incorporated herein by reference in their entirety. Such catalysts are commonly referred to as "superbases." See also P. Kisanga et al., *J. Org. Chem.*, 65 (2000). In one embodiment, the superbase used herein has the formula as shown in 1:

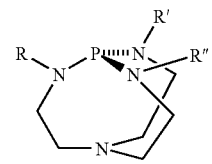

wherein R', R" and R'" are selected from the group consisting of H, $(C_1-C_8)$alkyl, preferably $(C_1-C_4)$alkyl and $(C_6-C_9)$ aryl, although it is known that R'=R"=R'"=H may be difficult to obtain. In one embodiment, R', R" and R'" are the same group. In a particular embodiment, R', R", R'" are each iso-Bu, i.e., the compound is $P(isoBuNCH_2CH_2)_3N$. In another embodiment, R', R" and R'" are each iso-Pr, such that the compound is $(P(isoPrNCH_2CH_2)_3N)$. In yet another embodiment, R', R" and R'" are each $CH_3$, such that the compound is $(P(CH_3NCH_2CH_2)_3N)$. These three commercially available superbases are exceptionally strong nonionic bases with pKa's of ca. 32 in acetonitrile and have superior catalytic activities for a wide variety of reactions including sequenced reactions, although the invention is not so limited.

Other catalysts useful herein include polymer-bound superbases as described in U.S. patent application Ser. No. 10/989,540, filed on Nov. 16, 2004, commonly assigned, in combination with palladium. In a particular embodiment, the polymer-bound superbase has the following formula:

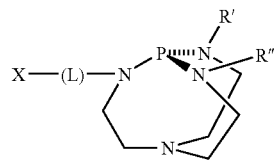

wherein R', R" and R'" are each H, $(C_1-C_8)$alkyl, $(C_6-C_9)$ aryl, or $(alk)_3Si$, wherein each alk is $(C_1-C_4)$alkyl; L is an organic linking moiety and X is a solid support material, such as a polymer, and the salts thereof.

In yet another embodiment, the superbase further includes up to twelve identical or different R groups (including $(C_1-C_8)$alkyl, $(C_1-C_4)$alkyl and $(C_6-C_9)$aryl) on the three $CH_2CH_2$ bridges from the PN nitrogens to the bottom nitrogen in either the polymer-free or polymer bound superbase described above. For example, the superbase having the formula of 1 as shown above may have additional groups V, W, X, Y and Z which can be identical or different R groups attached as shown below:

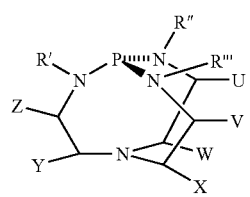

Known analogs of the various superbases described herein are still very strong base ligands and may be useful herein, in combination with palladium compounds.

All of the above described superbases are strong non-ionic bases as defined above, and, during the reactions, function essentially as "ligands" on the palladium compound. For the types of reactions of interest herein, an ionic base is also used. In one embodiment, sodium tert-butoxide (NaO-t-Bu) is used, although the invention is not so limited. It is possible that other ionic bases, such as other metal alkoxide bases, amide bases (e.g., metal amides), and the like, can also be used.

The reactions of interest which produce both styrenes and stilbenes operate sequentially at two different temperatures, respectively. The temperature difference needs to be large enough so that the higher temperature reaction or reactions (performed after the lower temperature reaction or reactions) do not occur at all or occur very slowly (i.e., causing impurity levels low enough such that the yields are still acceptable, i.e., at least competitive with known yields.

However, the temperature difference should not be so great such that the upper temperature is excessively high, as this can cause the components to decompose. The particular temperature difference used is dependent on the reaction conditions present and is generally limited by the solvent system being used, although in some embodiments, the reactions can be performed at higher temperatures under pressure. Testing can be performed with various starting materials, solvents, catalysts, and so forth, to determine optimal conditions. In one embodiment, the temperature difference is between about 40 and 60° C. In another embodiment the temperature difference is less than about 40° C., such as down to 30° C. or 20° C., although even smaller temperature differences may work under certain conditions. In other embodiments, the temperature difference is greater than 60° C., such as up to about 70° C. or 80° C. or more.

Exemplary temperatures used for the lower temperature reaction can range from about 20 to 80° C. In one embodiment the lower temperature reaction is one or more amination reactions performed at about 40 to 60° C. Exemplary temperatures used for the higher temperature reaction can range from about 40 to 150° C. or more. In one embodiment, the upper temperature reaction comprises at least one Heck reaction performed at about 100 to 120° C. In a particular embodiment, the lower temperature reaction is a Buchwald-Hartwig double amination reaction performed at about 60° C. and the higher temperature reaction is a Heck intermolecular reaction performed at about 110° C.

Varying the temperature can affect the total time needed for each reaction with the reactions generally taking longer at lower temperatures (typically the reaction speed doubles for about every 10° C. increase in temperature, although the invention is not so limited). The reaction times are also dependent on several other factors, including, but not limited to, concentration, type and amount of starting material, concentration, type and amount of catalyst, concentration and type of solvents and their relative amounts, reaction temperature, and so forth. In one embodiment, the lower temperature reaction takes from a few minutes up to about five (5) hours. In a particular embodiment, the lower temperature reaction is a double amination reaction which takes about one (1) to five (5) hrs. In a particular embodiment, the lower temperature reaction is a Buchwald-Hartwig double amination reaction which takes about three (3)hrs. In one embodiment, the upper temperature reaction takes from one (1) hr up to about 24 hrs or more.

In most embodiments, the reaction is performed in an inert atmosphere to maximize the yield, such as an atmosphere of nitrogen, argon, etc. Preferably the container in which the reaction is to be performed is flushed a suitable number of times with the gas being used. In one embodiment, the container is flushed at least about three times as is known in the art.

In the sequential reactions of interest herein, one or more solvents are used. Any suitable solvent can be used as long as it is compatible with the reaction components. In most or all embodiments, a non-polar solvent is used. In one embodiment, toluene is used. In other embodiments, hexane, xylene, tetrahydrofuran or the like, can be used. Typically the solvent is dried using conventional drying techniques known in the art. The solvent is preferably dried so it does not adversely impact the activity of the catalyst system. In a particular embodiment the solvent can be collected in a Grubbs-type solvent purification system made by Innovative Technologies having offices in Newburyport, Mass. A Grubbs system is an automated instrument for obtaining a set of dry solvents by passing each solvent through its own column containing a drying agent. In another embodiment, the solvent, such as toluene is obtained by distilling it from sodium as is known in the art.

Yields of the final products are preferably comparable to or better than yields from known methods. In one embodiment, the yield ranges from at least about 41% up to 99% or more, depending on the particular reaction sequence being run. In another embodiment, the yield is between about 81 and 98%. (See Tables 1-6 in Examples 1-6).

Embodiments of the present invention provide for one pot reactions which comprise one or more aminations of one or more aryl halide reagents and an arylation to produce an intermediate product and an end product or products. It is also possible that pseudohalide reagents (e.g., triflates) could be used. The aminations are generally performed at a first temperature and the arylation is performed at a second, higher temperature. By varying the type and location of the aryl groups on an amino styrene core the stoichiometry of the final product can be controlled.

In one embodiment, two single aminations are performed at a first temperature followed by an arylation reaction at a second, higher temperature with a single aryl halide reagent to produce a combination of intermediate styrene products and stilbene end products. (See Scheme 1). In another embodiment, two single aminations are performed at a first temperature with a first aryl halide reagent to produce an intermediate styrene product which is reacted with a second aryl halide reagent at a higher temperature to produce a stilbene end product. In other embodiments, the double amination is performed with two different aryl halides. (See Schemes 2 and 3). In some embodiments, the end products are symmetrically substituted diarylaminostilbenes. In other embodiments, the end products are unsymmetrically substituted diarylaminostilbenes. In some embodiments, the intermediate diarylaminostyrene products (symmetrical and unsymmetrical) are novel.

In one embodiment, the present invention comprises an amination reaction followed by an arylation reaction in one pot using a superbase catalyst combined with a palladium compound such as $Pd_2(dba)_3$. In one embodiment, the amination is a double amination reaction and the arylation is an intermolecular Heck arylation reaction. In one embodiment, the double amination is a sequence of two Buchwald-Hartwig amination reactions which produces aryl amines from aryl halides and primary or secondary amines. In a particular embodiment, the starting amine is a primary amine such as an aminostyrene. In this embodiment, the amination is preferably followed by an intermolecular Heck reaction, i.e., a C—C coupling between the aryl halide starting material and the styrenes produced as a result of the amination reaction, in the presence of the same palladium-superbase catalyst system.

In various embodiments, the present invention comprises a one pot synthesis of N,N-diarylaminostyrenes and N,N-diarylaminostilbenes from commercially available starting materials. In one embodiment, the starting materials include an aryl halide reagent and a primary amine, such as an aminostyrene.

In a particular embodiment, a trans-4-N,N-diarylaminostyrene is synthesized using a series of two Buchwald-Hartwig aminations followed by the synthesis of trans-4-N,N-diarylaminostilbenes from a subsequent intermolecular Heck reaction in the presence of $Pd_2(dba)_3$/P(isoBuNCH$_2$CH$_2$)$_3$N as the catalyst system. In one embodiment, 4-aminostyrene 2 is the starting material which is coupled with an aryl halide 3 such as bromobenzene or iodobenzene in the presence of $Pd_2(dba)_3$ and P(isoBuNCH$_2$CH$_2$)$_3$N in dry toluene under an argon atmosphere as shown in Scheme 1 below to produce a N,N-diarylaminostyrene and a trans-4-N,N-diarylaminostilbene. Additionally, NaO-t-Bu is also added as an ionic base to the reaction mixture together with the palladium compound, e.g., $Pd_{2(dba)3}$.

Scheme 1

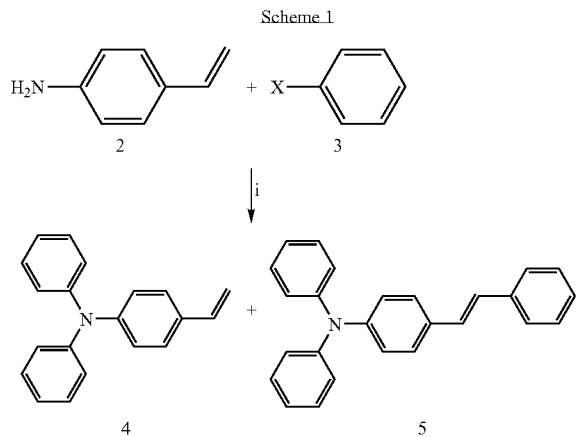

wherein i=Pd$_2$dba$_3$/P(isoBuNCH$_2$CH$_2$)$_3$N; X=halogen.

In an exemplary embodiment, i=2 mol % of Pd$_2$dba$_3$ and 4 mol % of P(isoBuNCH$_2$CH$_2$)$_3$N and X=I or Br. (See Example 1). Results of optimization studies performed under these conditions are shown in Table 1 of Example 1. For these experiments, the double amination reaction (which produced compound 4) was performed at about 60° C., while the Heck reaction (which produced compound 5) was performed at temperatures between about 100 and 110° C., although the invention is not so limited. Products which can be produced under Scheme 1 include, but are not limited to, 4-ethenyl-N,N-diphenylbenzenamine (4) and N,N-diphenyl-4-[2-phenylethenyl]benzenamine (5).

Other products which can be produced according to Scheme 1 include, but are not limited to, the products discussed in Example 2, which are produced by the reactions shown in Table 2. As discussed below, some of these products are novel. In these embodiments, aryl bromides other than bromobenzene are used as compound 3. In yet another embodiment, various aryl iodides are used as compound 3. In exemplary embodiments, various aryl bromides and aryl iodides are coupled with a styrene, such as 4-aminostyrene, in the presence of a palladium-proazaphosphatrane catalyst system. In one embodiment, these starting materials are combined in the presence of 2 mol % of Pd$_2$(dba)$_3$ and 4 mol % of P(isoBuNCH$_2$CH$_2$)$_3$N in dry toluene under an argon atmosphere. Results of studies performed under these conditions are shown in Table 2 of Example 2.

In all of the experiments performed in Examples 1 and 2 (Scheme 1), the double amination reaction was performed at about 60° C., while the Heck reaction was performed at temperatures between about 100 and 110° C., although the invention is not so limited. However, faster conversion was realized at the higher temperature of 110° C. for the reactions performed. This trend is expected to continue for other comparable reactions described herein, although optimization studies can be performed to strike a suitable balance between higher yields and increased energy costs due to higher temperatures. Yields were generally comparable to or better than yields obtained by conventional methods. At least this result is expected for comparable reactions described herein.

In another embodiment, a trans-4-N,N-diarylaminostilbene is synthesized using a series of two Buchwald-Hartwig aminations performed with a first aryl halide (I), followed by an intermolecular Heck arylation with a second aryl halide (II) in the presence of Pd$_2$(dba)$_3$/P(isoBuNCH$_2$CH$_2$)$_3$N as the catalyst system. The use of two different aryl halides allows different R groups (R$^1$ and R$^2$) to be present in the final product (6), to produce an unsymmetrically substituted N,N-diarylaminostilbene, although in this embodiment the same R's are present on the aryl groups bonded to the nitrogen. In a particular embodiment, the Buchwald-Hartwig aminations and subsequent intermolecular Heck reaction are carried out by adding varying amounts of 4-aminostyrene to a first aryl halide (I) in the presence of Pd$_2$(dba)$_3$/P(isoBuNCH$_2$CH$_2$)$_3$N as the catalyst system to produce reaction products as shown in Scheme 2. This reaction is followed by an intermolecular Heck arylation when a second aryl halide (II) is added, thus producing the end product (6) as shown. The two amination reactions take place at a first temperature, while the Heck reaction takes place at a second, higher temperature.

In a particular embodiment, 4-aminostyrene is the starting material which is coupled with a first aryl halide (I) such as bromobenzene or iodobenzene in the presence of Pd$_2$(dba)$_3$ and P(isoBuNCH$_2$CH$_2$)$_3$N in dry toluene under an argon atmosphere as shown in Scheme 2 below to produce a symmetrical intermediate diarylaminostyrene product. This product is used in a subsequent intermolecular Heck reaction performed at a second, higher temperature to produce an unsymmetrically substituted trans-4-N,N-diarylaminostilbene, i.e., all the phenyl groups bearing R substitutents are not identical. Additionally, NaO-t-Bu is also added as an ionic base to the reaction mixture.

Scheme 2

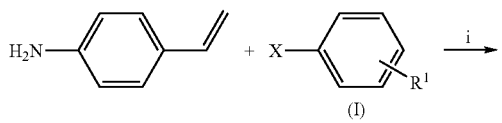

(I)

-continued

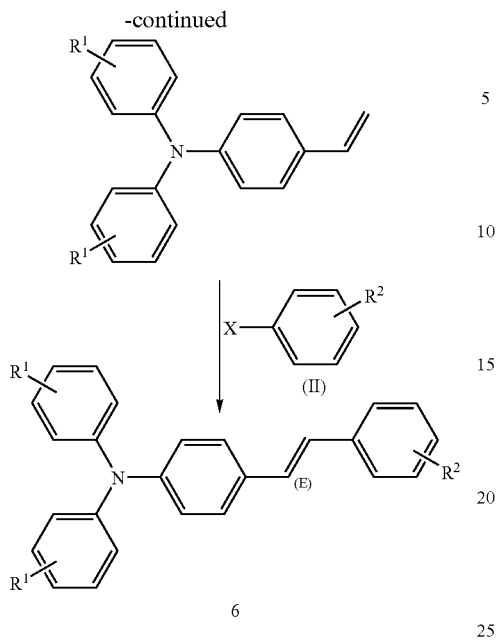

6 wherein i=Pd$_2$dba$_3$/P(isoBuNCH$_2$CH$_2$)$_3$N; X=halogen; and R, R$^1$ and R$^2$ can each be H, one or more (C$_1$-C$_8$)alkyl, one or more (C$_6$-C$_9$)aryl or one or more (C$_1$-C$_8$)alkoxy.

In particular embodiments, R$^1$ is selected from the group consisting of H, 4-OCH$_3$, 3-OCH$_3$, 3-CH$_3$ and 4-CH$_3$ while R$^2$ is selected from the group consisting of H, 4-CH$_3$, 3-CH$_3$ and 3-OCH$_3$. In an exemplary embodiment, i=2 mol % of Pd$_2$dba$_3$ and 4 mol % of P(isoBuNCH$_2$CH$_2$)$_3$N and X=I or Br. Products (6) which can be produced under Scheme 2 include, but are not limited to, N,N-diphenyl-4-[2-(4-methylphenyl) ethenyl]benzenamine (wherein R$^1$=H and R$^2$=CH$_3$) and N,N-bis(4-methoxyphenyl)-4-[2-phenylethenyl]benzenamine (wherein R$^1$=4-OCH$_3$ and R$^2$=H). Other products which can be produced according to Scheme 2 include, but are not limited to, the products produced by the reactions shown in Table 3. Yields were generally comparable to or better than yields obtained by conventional methods. (See Table 3). At least this result is expected for comparable reactions described herein. As discussed below, some of these products are novel.

In a similar manner, unsymmetrically N-substituted diarylaminostilbenes 7 can be synthesized in very good yields by changing the addition mode of arylhalides as depicted in Scheme 3 below. The use of two different aryl halides allows different R groups (R$^1$ and R$^2$) to be present on the aryl groups which are bonded to the nitrogen in the end product (7). The resulting product is unsymmetrical, i.e. again, all the phenyl groups bearing R substituents are not identical. In one embodiment, less expensive aryl chlorides can be used as aryl halide (I) for a single amination, i.e., mono amination, followed by the addition of the second aryl halide (II) to complete the reaction, although the invention is not so limited.

Scheme 3

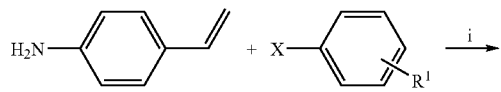

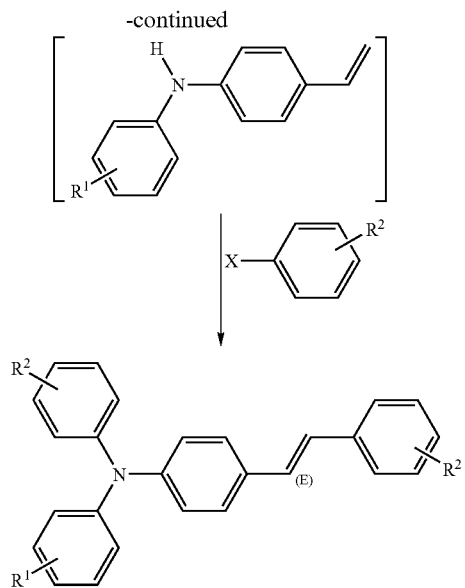

7 wherein i=Pd$_2$dba$_3$/P(isoBuNCH$_2$CH$_2$)$_3$N; X =halogen; and R, R$^1$ and R$^2$ can each be H, one or more (C$_1$-C$_8$)alkyl, one or more (C$_6$-C$_9$)aryl or one or more (C$_1$-C$_8$)alkoxy.

In a particular embodiment, R$^1$ is selected from the group consisting of 4-CH$_3$, 4-OCH$_3$, 3-OCH$_3$, 4-tert-butyl and R$^2$ is selected from the group consisting of H, 4-CH$_3$, 3-CH$_3$ and 4-Cl. In an exemplary embodiment, i=2 mol % of Pd$_2$dba$_3$ and 4 mol % of P(isoBuNCH$_2$CH$_2$)$_3$N and X=I, Cl or Br. Products (7) which can be produced under Scheme 3 include, but are not limited to, N-(4-methylphenyl)-N-(Phenyl)-4-[2-phenylethenyl]benzenamine (wherein R$^1$=CH$_3$, R$^2$=H) and N-(4-methoxyphenyl)-N-(Phenyl)-4-[2-phenylethenyl]benzenamine (wherein R$^1$=4-OCH$_3$, R$^2$=H). (See Table 4).

Symmetrically substituted N,N-diarylaminostyrenes, which are useful as intermediates in the sequential reactions described herein, can also be produced by a double amination reaction using a single type of aryl halide which combines with the starting amine to produce symmetrically substituted aryl groups on the nitrogen of the resulting N,N-diarylaminostyrene. See Scheme 4 below:

Scheme 4

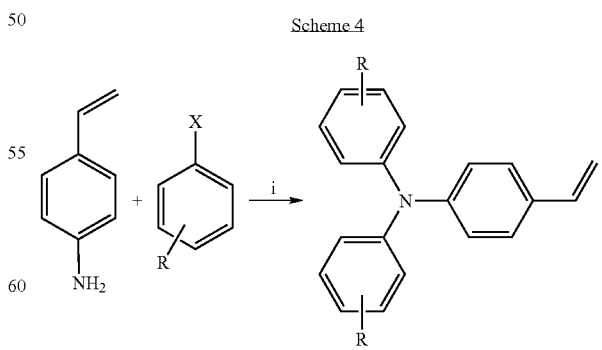

wherein i=Pd$_2$dba$_3$/P(isoBuNCH$_2$CH$_2$)$_3$N; X=halogen; and R can each be H, one or more (C$_1$-C$_8$)alkyl, one or more (C$_6$-C$_9$)aryl or one or more (C$_1$-C$_8$)alkoxy.

In one embodiment, R is selected from the group consisting of H, 4-CH$_3$, 3-CH$_3$, 4-tertbutyl, 4-Cl, 3,5-dimethyl and naphthyl. In an exemplary embodiment, i=2 mol % of Pd$_2$dba$_3$ and 4 mol % of P(isoBuNCH$_2$CH$_2$)$_3$N and X═I or Br. Products which can be produced under Scheme 4 include, but are not limited to, 4-ethenyl-N,N-diphenylbenzenamine (wherein R$^1$═R$^2$═H) and 4-ethenyl-N,N-bis(4-methoxyphenyl)benzenamine (wherein R$^1$═R$^2$═OCH$_3$). Other products which can be produced according to Scheme 4 include, but are not limited to, the products produced by the reactions shown in Table 5. Yields were generally comparable to or better than yields obtained by conventional methods. (See Table 5). At least this result is expected for comparable reactions described herein. As discussed below, some of these intermediate products are novel and can further be used in additional reactions, such as a subsequent arylation to produce N,N-diarylaminostilbenes which are useful in a number of applications as described herein.

Unsymmetrically substituted N,N-diarylaminostyrenes which are useful as intermediates in the sequential reactions described herein, can also be produced by a double amination reaction using two different aryl halides which combine with the starting amine to produce unsymmetrically substituted aryl groups on the nitrogen of the resulting N,N-diarylaminostyrene. See Scheme 5 below:

Scheme 5

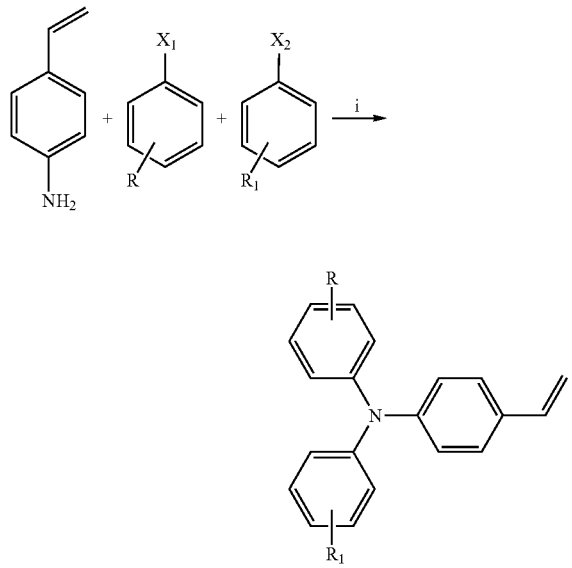

wherein i=Pd$_2$dba$_3$/P(isoBuNCH$_2$CH$_2$)$_3$N; X$_1$═X$_2$═halogen; and R, R$^1$ and R$^2$ can each be H, one or more (C$_1$-C$_8$)alkyl, one or more (C$_6$-C$_9$)aryl or one or more (C$_1$-C$_8$)alkoxy.

In one embodiment, the X$_1$═X$_2$. In another embodiment, X$_1$≠X$_2$. In a particular embodiment, X$_1$═Br and X$_2$═Cl. Yields were average to quite good for the compounds produced, ranging from about 68 to 86%. (See Table 6). At least this result or possibly better yields may occur for comparable reactions described herein. As discussed below, all of the products produced to date by Scheme 5 are novel and can further be used in additional reactions, such as a subsequent arylation or a subsequent amination and an arylation to produce N,N-diarylaminostilbenes which are useful in a number of applications as described herein.

The end products, namely the N,N-diarylaminostilbenes, produced according to the methods described herein may take on a number of configurations, but can generally be described as:

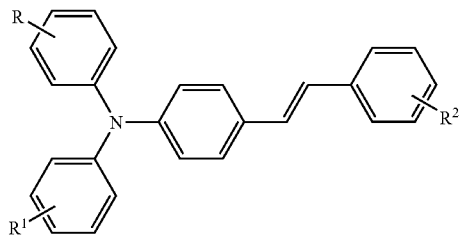

wherein R, R$^1$ and R$^2$ can each be H, one or more (C$_1$-C$_8$) alkyl, one or more (C$_6$-C$_9$)aryl or one or more (C$_1$-C$_8$) alkoxy.

It is possible the end products may have additional configurations with other substituents present, beyond those noted above. In particular embodiments, R═R$^1$═H, 4-CH$_3$ 3-CH$_3$, 3-OCH$_3$ or 4-OCH$_3$ and R$^2$═4-CH$_3$, 3-CH$_3$, 3-OCH$_3$, 4-OCH$_3$ or 3,5-dimethyl. In other embodiments, R═R$^1$═R$^2$═H, 4-CH$_3$, 3-CH$_3$, 2-CH$_3$, 3-OCH$_3$, 4-OCH$_3$, 4-Cl, 4-tert-butyl or 3,5-dimethyl. In yet other embodiments, R$^1$═R$^2$═H, 4-CH$_3$, 3-CH$_3$ or Cl and R═4-CH$_3$, 4-OCH$_3$, 3-OCH$_3$, 4-tert-butyl or 3-CH$_3$.

In one embodiment, the products are intermediate styrene products (4) and stilbene end products (5), which include, but are not limited to, (4) 4-ethenyl-N,N-diphenylbenzenamine and (5) N,N-diphenyl-4-[2-phenylethenyl]benzenamine (See Table 1). In another embodiment, the products include, but are not limited to, (4) 4-ethenyl-N,N-bis(4-methylphenyl)benzenamine and/or (5) N,N-bis(4-methylphenyl)-4-[2-(4-methylphenyl)ethenyl]benzenamine; (4) 4-ethenyl-N,N-bis(3-methylphenyl)benzenamine and (5) N,N-bis(3-methylphenyl)-4-[2-(3-methylphenyl)ethenyl] benzenamine; (4) 4-ethenyl-N,N-bis(4-methoxyphenyl)benzenamine and/or (5) N,N-bis(4-methoxyphenyl)-4-[2-(4-methoxyphenyl)ethenyl]benzenamine (See Table 2).

In one embodiment, the products are stilbene end products (6) which include, but are not limited to, N,N-diphenyl-4-[2-(4-methylphenyl) ethenyl]benzenamine; N,N-bis(4-methoxyphenyl)-4-[2-phenylethenyl]benzenamine; N,N-bis(4-methylphenyl)-4-[2-phenylethenyl]benzenamine; N,N-bis(3-methylphenyl)-4-[2-phenylethenyl]benzenamine; N,N-bis(4-methoxyphenyl)-4-[2-(4-methylphenyl)ethenyl] benzenamine; and N,N-bis(4-methylphenyl)-4-[2-(3-methoxyphenyl)ethenyl]benzenamine. (See Table 3).

In one embodiment, the products are stilbene end products (7) which include, but are not limited to, N-(4-methylphenyl)-N-(Phenyl)-4-[2-phenylethenyl]benzenamine and N-(4-methoxyphenyl)-N-(Phenyl)-4- [2-phenylethenyl]benzenamine. (See Table 4).

In one embodiment, the products are intermediate styrene products which include, but are not limited to, 4-ethenyl-N,N-diphenylbenzenamine (Entry 1); 4-ethenyl-N,N-bis(4-methylphenyl)benzenamine; 4-ethenyl-N,N-bis(3- methylphenyl)benzenamine; and 4-ethenyl-N,N-bis(naphthyl) benzenamine (Entry 7). (See Table 5).

Yet other embodiments of the invention produce novel stilbene compounds. Such products may take on a number of configurations, but can generally be described as:

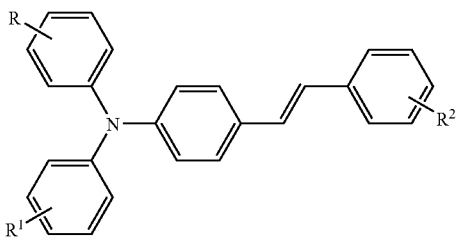

wherein R, R$^1$ and R$^2$=3,5-dimethyl, 3-CH$_3$, 3-CH$_3$-4-OCH$_3$ or 3-OCH$_3$; or R=R$^1$=3-OCH$_3$ and R$^2$=H; or R=R$_1$=4-OCH$_3$ and R$^2$=3-CH$_3$.

In one embodiment, the novel products include both intermediate (4) styrene products and stilbene end products (5) which include, but are not limited to, a novel compound 4, namely, 4-ethenyl-N,N-bis(3,5-dimethylphenyl)benzenamine and a novel compound 5, namely, N,N-bis(3,5-dimethylphenyl)-4-[2-(3,5dimethylphenyl)ethenyl]benzenamine;a novel compound 4, namely, 4-ethenyl-N,N-bis(3-methyl-4-methoxyphenyl)benzenamine and a novel compound 5, namely, N,N-bis(3-methyl-4-methoxyphenyl)-4-[2-(3-methyl-4-methoxyphenyl) ethenyl]benzenamine; a novel compound 4, namely, 4-ethenyl-N,N-bis(3-methoxyphenyl)benzenamine and a novel compound 5, namely, N,N-bis(3-methoxyphenyl)-4-[2-(3-methoxyphenyl) ethenyl]benzenamine. In a particular embodiment, these products are produced according to Scheme 1. (See Entries, 2, 3, 4, 6 and 7 of Table 2).

In one embodiment, the novel products are stilbene end products which include, but are not limited to, a novel compound 6, namely, N,N-bis(3-methoxyphenyl)-4-[2-phenylethenyl]benzenamine N,N-bis(4-methoxyphenyl)-4-[2-(3-methylphenyl)ethenyl]benzenamine, produced according to Scheme 2. (See Entries 6 and 9 of Table 3).

Novel intermediate products, i.e., N,N-diarylaminostyrenes have also been produced herein. Such products may take on a number of configurations, but can generally be described as:

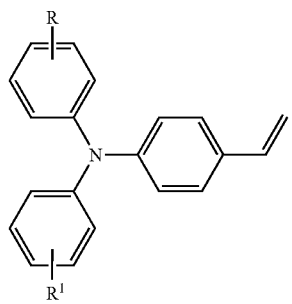

wherein R=R$^1$=3,5-dimethyl, 3CH$_3$, 3-CH$_3$-4-OCH$_3$, 4-tert-butyl or 4-Cl, or R$^1$=4-CH$_3$ and R=4-OCH$_3$ or 3CH$_3$, or R$^1$=3-OCH$_3$ and R=4CH$_3$.

In one embodiment, the novel intermediate styrene products include, but are not limited to, 4-ethenyl-N,N-bis(3,5-dimethylphenyl)benzenamine; 4-ethenyl-N,N-bis(4-ter-butylphenyl)benzenamine and 4-ethenyl-N,N-bis(4-chlorophenyl)benzenamine. (See Entries 4, 5 and 6 of Table 5). In a particular embodiment, these products are produced according to Scheme 4 described herein. (See Table 5).

In one embodiment, the novel intermediate styrene products include, but are not limited to, 4-ethenyl-N-(4-methoxyphenyl)-N-(4-methylPhenyl)benzenamine; 4-ethenyl-N-(3-methylphenyl)-N-(4-methylPhenyl)benzenamine; and 4-ethenyl-N-(3-methoxyphenyl)-N-(4-methylPhenyl)benzenamine). In a particular embodiment, these products are produced according to Scheme 5 described herein. (See Table 6).

The invention will be further described by reference to the following examples, which are offered to further illustrate various embodiments of the present invention. It should be understood, however, that many variations and modifications may be made while remaining within the scope of the present invention.

EXAMPLE 1

All reactions were performed under an atmosphere of argon in oven dried glassware. Toluene was collected from a Grubbs type solvent purification system (Innovative Technologies) and stored over 4 Å molecular sieves. $^1$H and $^{13}$C NMR spectra were recorded on Varian VXR 300 MHz NMR spectrometer. NMR spectra were obtained using CHCl$_3$-d as solvent. Chemical shifts are given in the δ scale with tetramethylsilane or the CHCl$_3$ proton at 7.23 as the internal standard. Mass spectra were recorded on a Kratos MS-50 mass spectrometer.

Starting materials for all examples were obtained from Sigma-Aldrich, having offices in Saint Louis, Mo. The purities ranged from 97 to 99%. Specifically isobutylproazaphosphatrane (P(isoBuNCH$_2$CH$_2$)$_3$N), 4-aminostyrene (4-vinylaniline), 5-bromo-m-xylene and NaO-t-Bu were approximately 97% pure. Iodobenzene, 4-bromotoluene, 3-bromotoluene, 4-bromo-2-methylanisole and 4-iodoanisole were all approximately 98% pure. 3-bromoanisole was 98+% pure. Bromobenzene, 4-bromoanisole, 3-iodoanisole and 4-iodotoluene were all approximately 99% pure. Other compounds were obtained were at least about 98% pure.

The structural formulations of the products produced were characterized by $^1$H, $^{13}$C and HR mass spectra (shown below) and also by comparison with spectra reported in the literature for known compounds with which they correlated very well.

General Procedure for the one Pot Synthesis of N,N-diphenylaminostyrenes (4) and trans-4-N,N-diarylaminostilbenes (5)

An oven dried Schlenk tube equipped with a magnetic stirring bar was charged with Pd$_2$dba$_3$ (2 mol %) and NaO-t-Bu (3.5 mmol). The tube was capped with a rubber septum, evacuated and then flushed with argon three times. P(isoBuNCH$_2$CH$_2$)$_3$N (4 mol %) was then added via syringe. 4-aminostyrene (1 mmol), aryl halide (3.2 mmol) and toluene (10 mL) were then successively added via syringe. The tube was heated at the temperature and for the time specified in Table 1. After the reaction was complete, as judged by TLC, the reaction mixture was cooled to room temperature. The reaction mixture was filtered through a celite pad to remove solid impurities and the filtrate was concentrated in vacuo. The crude products were purified by column chromatography using EtOAc/hexane mixtures as eluants to afford the coupled products as is known in the art.

The general procedure as described above was performed according to Scheme 1 shown above with Pd$_2$dba$_3$ (18.3 mg, 2 mol %), NaO-t-Bu (336 mg, 3.5 mmol), P(isoBuNCH$_2$CH$_2$)$_3$N (13.6 mg, 4 mol %), 4-aminostyrene (119 mg, 1 mmol), 10 mL of dry toluene, and either bromobenzene (502 mg, 3.2 mmol)or iodobenzene (653 mg, 3.2 mmol).

The reactions were run at varying temperatures and times and produced N, N-diphenylaminostyrenes such as 4-ethenyl-N,N-diphenylbenzenamine as a colorless solid and trans-4-N, N-diphenylaminostilbenes, such as N,N-diphenyl-4-[2-phenylethenyl]benzenamine as a yellow solid after chromatography with hexane in the amounts and yields shown in Table 1.

Results

TABLE 1

Optimization of the one pot Buchwald-Hartwig aminations/intermolecular Heck reaction

| Entry | aryl halide | Time (h) | T (° C.) | Yield %[a] 4 | 5 | Total yield 4 + 5 |
|---|---|---|---|---|---|---|
| 1 | ⌬—Br | 3 | 60° C. | 90 | 0 | 90 |
| 2 | | 12 | 100° C. | 92 | 2 | 94 |
| 3 | | 16 | 110° C. | 9 | 83 | 92 |
| 4 | ⌬—I | 12 | 100° C. | 32 | 66 | 98 |
| 5 | | 24 | 100° C. | 0 | 94 (78)[b] | 94 |
| 6 | | 16 | 110° C. | 0 | 93 | 93 |

[a]Isolated yield.
[b]Literature yield for a two-pot synthesis.
4 = types of N,N-diphenylaminostyrenes;
5 = types of trans-4-N,N-diphenylaminostilbenes Because the amination reactions in the above experiments were completed within 3 h at 60° C. while the Heck reactions required a higher temperature and a longer reaction time, the difference in coupling activity can be used for the one pot synthesis of product 5 with two identical aryl groups on nitrogen and a different one on the opposite terminus of the product.

It was found under the conditions of Entry 1 in Table 1 above, the only coupling observed was double amination. The Heck reaction required a minimum of 110° C. for bromobenzene for protocol efficiency (see Entries 2 and 3 in Table 1). Although the Heck reaction did occur at 100° C. for iodobenzene (Entries 4 and 5), faster conversion was realized at 110° C. for this transformation (Entry 6).

The products produced according to the various reactions shown in Table 1 are noted below.

Spectral Data for Table 1

(4) 4-ethenyl-N,N-diphenylbenzenamine
(Entries 1-6)

$^1$H NMR (300 MHz, CDCl$_3$): δ 5.13 (d, J=10.86 Hz, 1H), 5.61 (d, J=17.58 Hz, 1H), 6.61 (dd, J$_1$=10.86 Hz, J$_2$=17.58 Hz, 1H), 7.01-7.10 (m, Ar, 8H), 7.21-7.27 (m, Ar, 6H). $^{13}$C NMR (75 MHz, CDCl$_3$): δ 112.34, 123.12, 123.81, 124.57, 127.25, 129.45, 132.07, 136.42, 147.68, 147.80. m.p. 90-92° C. HRMS: Cald. for C$_{20}$H$_{17}$N (M$^+$) 271.1361, Found: 271.1359.

(5) N,N-diphenyl-4-[2-phenylethenyl]benzenamine
(Entries 2-6)

$^1$H NMR (300 MHz, CDCl$_3$): δ 7.04-7.15 (m, 10H), 7.26-7.31 (m, 5H), 7.34-7.42 (m, 4H), 7.50 (d, J=7.32 Hz, 2H). $^{13}$C NMR (75 MHz, CDCl$_3$): δ 123.27, 123.85, 124.72, 126.56, 127.29, 127.53, 127.61, 128.41, 128.91, 129.54, 131.67, 137.86, 147.60, 147.79. m.p. 152-154° C. HRMS: Cald. for C$_{26}$H$_{21}$N (M$^+$) 347.1674, Found: 347.1681.

EXAMPLE 2

The general procedure for the one pot synthesis of N,N-diphenylaminostyrenes (4) and trans-4-N,N-diarylaminostilbenes (5) described in Example 1 was followed. To test the methodology more generally, the coupling of a variety of aryl bromides and iodides with 4-aminostyrene was performed according to Scheme 1 with the results shown in Table 2 below.

Following the general procedure shown above, Pd$_2$dba$_3$ (18.3 mg, 2 mol %), NaO-t-Bu (336 mg, 3.5 mmol), P(isoBuNCH$_2$CH$_2$)$_3$N (13.6 mg, 4 mol %), 4-aminostyrene (119 mg, 1 mmol), 4-bromotoluene (547 mg, 3.2 mmol), and 10 mL of dry toluene at 110° C. for 16 h produced (4) 4-ethenyl-N,N-bis(4-methylphenyl)benzenamine (32 mg, 11%) as a viscous liquid and (5) N,N-bis(4-methylphenyl)-4-[2-(4-methylphenyl)ethenyl]benzenamine (325 mg, 84%) as a yellow solid after chromatography with 1% EtOAc/hexane mixture. Total yield=95%. (See Entry 1 of Table 2).

Following the general procedure, Pd$_2$dba$_3$ (18.3 mg, 2 mol %), NaO-t-Bu (336 mg, 3.5 mmol), P(isoBuNCH$_2$CH$_2$)$_3$N (13.6 mg, 4 mol %), 4-aminostyrene (119 mg, 1 mmol), 5-bromo-m-xylene (592 mg, 3.2 mmol), and 10 mL of dry toluene at 110° C. for 16 h produced a novel compound 4, namely, 4-ethenyl-N,N-bis(3,5-dimethylphenyl)benzenamine (124 mg, 37%) as a colorless solid and a novel compound 5, namely, N,N-bis(3,5-dimethylphenyl)-4-[2-(3,5-dimethylphenyl)ethenyl]benzenamine (262 mg, 61%) as a yellow solid after chromatography with 1% EtOAc/hexane mixture. Total yield=98%. (See Entry 2 of Table 2).

Following the general procedure, Pd$_2$dba$_3$ (18.3 mg, 2 mol %), NaO-t-Bu (336 mg, 3.5 mmol), P(isoBuNCH$_2$CH$_2$)$_3$N(13.6 mg, 4 mol %), 4-aminostyrene (119 mg, 1 mmol), 3-bromotoluene (547 mg, 3.2 mmol), and 10 mL of dry toluene at 110° C. for 16 h produced a novel compound 4, namely, 4-ethenyl-N,N-bis(3-methylphenyl)benzenamine (84 mg, 28%) as a viscous liquid and a novel compound 5, namely, N,N-bis(3-methylphenyl)-4-[2-(3-dimethylphenyl)ethenyl]benzenamine (232 mg, 60%) as a yellow solid after chromatography with 1% EtOAc/hexane mixture. Total yield=88%. (See Entry 3 of Table 2).

Following the general procedure, Pd$_2$dba$_3$ (18.3 mg, 2 mol %), NaO-t-Bu (336 mg, 3.5 mmol), P(isoBuNCH$_2$CH$_2$)$_3$N (13.6 mg, 4 mol %), 4-aminostyrene (119 mg, 1 mmol), 4-bromo-2-methyl-anisole (643 mg, 3.2 mmol), and 10 mL of dry toluene at 110° C. for 16 h produced a novel compound 4, namely, 4-ethenyl-N,N-bis(3-methyl-4-methoxyphenyl)benzenamine (95 mg, 27%) as a viscous liquid and a novel compound 5, namely, N,N-bis(3-methyl-4-methoxyphenyl)-4-[2-(3-methyl-4-methoxyphenyl) ethenyl]benzenamine (284 mg, 59%) as a viscous yellow liquid after chromatography with 1-5% EtOAc/hexane mixture. Total yield=86%. (See Entry 4 of Table 2).

Following the general procedure, Pd$_2$dba$_3$ (18.3 mg, 2 mol %), NaO-t-Bu (336 mg, 3.5 mmol),P(isoBuNCH$_2$CH$_2$)$_3$N (13.6 mg, 4 mol %), 4-aminostyrene (119 mg, 1 mmol), 4-bromoanisole (598 mg, 3.2 mmol), and 10 mL of dry toluene at 110° C. for 16 h produced (4) 4-ethenyl-N,N-bis(4-methoxyphenyl)benzenamine (157 mg, 47%) as a viscous liquid and (5) N,N-bis(4-methoxyphenyl)-4-[2-(4-methoxyphenyl)ethenyl]benzenamine (148 mg, 34%) as a yellow solid after chromatography with 1-5% EtOAc/hexane mixture. Total yield=81%. (See Entry 5 of Table 1).

Following the general procedure, $Pd_2dba_3$ (18.3 mg, 2 mol %), NaO-t-Bu (336 mg, 3.5 mmol), $P(isoBuNCH_2CH_2)_3N$ (13.6 mg, 4 mol %), 4-aminostyrene (119 mg, 1 mmol), 3-bromoanisole (598 mg, 3.2 mmol), and 10 mL of dry toluene at 110° C. for 16 h produced a novel compound 4, namely, 4-ethenyl-N,N-bis(3-methoxyphenyl)benzenamine (199 mg, 60%) and a novel compound 5, namely, N,N-bis(3-methoxyphenyl)-4-[2-(3-methoxyphenyl) ethenyl]benzenamine (147 mg, 34%) after chromatography with 1-5% EtOAc/hexane mixture. Total yield=94%. (See Entry 6 of Table 1).

Following the general procedure, $Pd_2dba_3$ (18.3 mg, 2 mol %), NaO-t-Bu (336 mg, 3.5 mmol), (13.6 mg, 4 mol %), 4-aminostyrene (119 mg, 1 mmol), 3-iodoanisole (749 mg, 3.2 mmol), and 10 mL of dry toluene at 110° C. for 16 h produced a novel compound 4, namely, 4-ethenyl-N,N-bis(3-methoxyphenyl)benzenamine (106 mg, 32%) and a novel compound 5, namely, N,N-bis(3-methoxyphenyl)-4-[2-(3-methoxyphenyl) ethenyl]benzenamine (277 mg, 63%) after chromatography with 1-5% EtOAc/hexane mixture. Total yield=95%. (See Entry 7 of Table 1).

Following the general procedure, $Pd_2dba_3$ (18.3 mg, 2 mol %), NaO-t-Bu (336 mg, 3.5 mmol), $P(isoBuNCH_2CH_2)_3N$ (13.6 mg, 4 mol %), 4-aminostyrene (119 mg, 1 mmol), 4-iodoanisole (749 mg, 3.2 mmol), and 10 mL of dry toluene at 110° C. for 16 h produced (5) N,N-bis(4-methoxyphenyl)-4-[2-(4-methoxyphenyl) ethenyl]benzenamine (180 mg, 41%) as the sole product after chromatography with 1-5% EtOAc/hexane mixture. (See Entry 8 of Table 2).

Following the general procedure, $Pd_2dba_3$ (18.3 mg, 2 mol %), NaO-t-Bu (336 mg, 3.5 mmol), $P(isoBuNCH_2CH_2)_3N$ (13.6 mg, 4 mol %), 4-aminostyrene (119 mg, 1 mmol), 4-Iodotoluene (698 mg, 3.2 mmol), and 10 mL of dry toluene at 110° C. for 16 h. produced (5) N,N-bis(4-methylphenyl)-4-[2-(4-methylphenyl) ethenyl]benzenamine (338 mg, 87%) as the sole product after chromatography with 1% EtOAc/hexane mixture. (See Entry 9 of Table 2).

Results

TABLE 2

One pot Buchwald-Hartwig aminations/intermolecular Heck reactions of 4-aminostyrene with aryl bromides and aryl iodides

| Entry | Aryl halide | Yield %[a] 4 | 5 | Total yield % [4 + 5] |
|---|---|---|---|---|
| 1 | (4-Me-C6H4-Br) | 11 | 84 | 95 |
| 2 | (3,5-diMe-C6H3-Br) | 37* | 61 | 98* |
| 3 | (3-Me-C6H4-Br) | 28 | 60 | 88* |
| 4 | (3-Me-4-MeO-C6H3-Br) | 27* | 59 | 86* |
| 5 | (4-MeO-C6H4-Br) | 47 | 34 | 81 |
| 6 | (3-MeO-C6H4-Br) | 60* | 34 | 94* |
| 7 | (3-MeO-C6H4-I) | 32* | 63 | 95* |
| 8 | (4-MeO-C6H4-I) | 0 | 41 | 41 |
| 9 | (4-Me-C6H4-I) | 0 | 87 (83%)[b] | 87 |

[a]Isolated yield. Reaction conditions: $Pd_2(dba)_3$ (2 mol %), 1 (4 mol %), NaO-t-Bu (3.5 equiv), aryl halides (3.2 equiv), 10 mL of toluene, 110° C., 16 h.
[b]literature yield.
*novel compounds In all cases, except for Entries 5 and 6, the major product formed was trans-N,N-diarylaminostilbenes [5]. The yields of 5 in Entries 1 and 9 are comparable to known yields, while the yield for 5 in Entries 5 and 8 are less than satisfactory. However, the yields of 5 in Entries 1 and 9 are superior to the overall yield (55%) for a three-step multi-pot procedure involving an Ullmann, Vilsmeier and Wittig reaction series.

The products produced according to the various reactions shown in Table 2 are noted below. The products produced according to the reactions shown in Entries 2, 3, 4, 6 and 7 are novel. Yields of the novel products are very good, ranging from about 86 to 98%.

Spectral Data for Table 2
  Entries 1 and 9:

(4) 4-ethenyl-N,N-bis(4-methylphenyl)benzenamine (Entry 1 only)

$^1$H NMR (300 MHz, $CDCl_3$): δ 2.29 (s, 6H), 5.09 (d, J=11.1 Hz, 1H), 5.56 (d, J=17.58 Hz, 1H), 6.58 (dd, $J_1$=10.86 Hz, $J_2$=17.58 Hz, 1H), 6.94-7.06 (m, 10 H), 7.22-7.25 (m, 2 H). $^{13}$C NMR (75 MHz, CDCl$_3$): δ 20.80, 111.56, 122.35, 124.61, 126.87, 129.84, 130.91, 132.53, 136.27, 145.13, 147.87. HRMS: Cald. for C$_{22}$H$_{21}$N (M$^+$) 299.1674, found: 299.16800.

(5) N,N-bis(4-methylphenyl)-4-[2-(4-methylphenyl) ethenyl]benzenamine $^1$H NMR (300 MHz, CDCl$_3$): δ 2.31 (s, 6H), 2.34 (s, 3H), 6.96-7.15 (m, 14 H), 7.32-7.39 (m, 4H). $^{13}$C NMR (75 MHz, CDCl$_3$): δ 20.81, 21.21, 122.46, 124.63, 126.12, 126.47, 127.06, 127.27, 129.31, 129.85, 130.80, 132.56, 134.90, 136.95, 145.10, 147.54. mp. 133-135° C. HRMS: Cald. for C$_{29}$H$_{27}$N (M$^+$) 389.21435, Found: 389.21510.

Entry 2 (Novel Compounds):

(4) 4-ethenyl-N,N-bis(3,5-dimethylphenyl)benzenamine, R=R$^1$=3,5-dimethyl $^1$H NMR (300 MHz, CDCl$_3$): δ 2.23 (s, 12H), 5.12 (d, J=10.86 Hz, 1H), 5.60 (d, J=17.56 Hz, 1H), 6.68-6.71 (m, 7H), 6.97 (d, J=8.55 Hz, 2H), 7.26 (d, J=8.67 Hz, 1H). $^{13}$C NMR (75 MHz, CDCl$_3$): δ 21.54, 111.96, 122.68, 123.46, 125.04, 127.11, 131.35, 136.55, 139.02, 147.83, 148.17. mp. 155-157° C. HRMS: Cald. for C$_{24}$H$_{25}$N (M$^+$) 327.1987, Found: 327.1978.

(5) N,N-bis(3,5-dimethylphenyl)-4-[2-(3,5-dimethylphenyl) ethenyl]benzenamine, R=R$^1$=R$^2$=3,5-dimethyl $^1$H NMR (300 MHz, CDCl$_3$): δ 2.22 (s, 12H), 2.32 (s, 6H), 6.68-6.72 (m, 6H), 6.87 (s, 1H), 6.95-7.00 (m, 4H), 7.11 (s, 2H), 7.33 (d, J=8.55 Hz, 2H). $^{13}$C NMR (75 MHz, CDCl$_3$): δ 21.29, 122.50, 123.22, 124.15, 124.85, 126.83, 127.09, 127.86, 128.98, 130.95, 137.60, 138.03, 138.79, 147.54, 147.65. mp. 150-152° C. HRMS: Cald. for C$_{32}$H$_{33}$N (M$^+$) 431.26130, Found: 431.26200.

Entry 3:

(4) 4-ethenyl-N,N-bis(3-methylphenyl)benzenamine $^1$H NMR (300 MHz, CDCl$_3$): δ 2.25 (s, 6H), 5.12 (d, J=10.86 Hz, 1H), 5.59 (d, J=17.58 Hz, 1H) 6.60 (dd, $J_1$=10.98 Hz, $J_2$=17.58 Hz, 1H), 6.82-6.90 (m, 6H), 6.98-7.01 (m, 2H), 7.10-7.05 (m, 2H), 7.25-7.28 (m, 2H). $^{13}$C NMR (75 MHz, CDCl$_3$): δ 21.63, 112.13, 121.88, 123.62, 123.99, 125.32, 127.17, 129.21, 131.69, 136.48, 139.27, 147.81, 147.91. HRMS: Cald. for C$_{22}$H$_{21}$N (M$^+$) 299.16740, Found: 299.16704.

Entry 3 (novel compound):

(5) N,N-bis(3-methylphenyl)-4-[2-(3-methylphenyl) ethenyl]benzenamine, R=R$^1$=R$^2$=3-CH$_3$ $^1$H NMR (300 MHz, CDCl$_3$): δ 2.24 (s, 6H), 2.34 (s, 3H), 6.81-6.83 (m, 2H), 6.87-6.92 (m, 4H), 6.96-7.03 (m, 4H), 7.09-7.20 (m, 4H), 7.25-7.28 (m, 2H), 7.35-7.36 (m, 2H). $^{13}$C NMR (75 MHz, CDCl$_3$): δ 21.61, 121.96, 123.60, 123.66, 124.06, 125.38, 127.17, 127.43, 128.19, 128.25, 128.72, 129.23, 131.44, 137.79, 138.30, 139.26, 147.69, 147.75. mp. 82-84° C. HRMS: Cald. for C$_{29}$H$_{27}$N (M$^+$) 389.21435, Found: 389.21493.

Entry 4 (Novel Compounds):

(4) 4-ethenyl-N,N-bis(3-methyl-4-methoxyphenyl) benzenamine, R=R$^1$=3CH$_3$-4-OCH$_3$ $^1$H NMR (300 MHz, CDCl$_3$): δ 2.05 (s, 6H), 3.79 (s, 6H), 5.03 (d, J=11.01 Hz, 1H), 5.51 (d, J=17.61 Hz, 1H), 6.50-6.76 (m, 7H), 6.92 (d, J=8.67 Hz, 2H), 7.17-7.25 (m, 2H). $^{13}$C NMR (75 MHz, CDCl$_3$): δ55.56, 110.54, 112.39, 116.78, 118.13, 127.09, 128.81, 128.86, 136.48, 136.69, 139.04, 149.07, 156.96. HRMS: Cald. For C$_{24}$H$_{25}$NO$_2$ (M$^+$) 359.18853, Found: 359.18904.

(5) N,N-bis(3-methyl-4-methoxyphenyl)-4-[2-(3-methyl-4-methoxyphenyl) ethenyl]benzenamine, R=R$^1$=R$^2$=3CH$_3$-4-OCH$_3$ $^1$H NMR (300 MHz, CDCl$_3$): δ 2.08 (s, 6H), 2.39 (s, 3H), 3.80 (s, 9H), 6.55 (d, J=8.67 Hz, 2H), 6.68-6.78 (m, 7H), 6.84 (s, 1H), 6.94-6.97 (d, J=8.67 Hz, 2H), 7.26-7.30 (m, 2H), 7.48 (d, J=8.43 Hz, 1H). $^{13}$C NMR (75 MHz, CDCl$_3$): δ 19.31, 20.40, 55.53, 111.88, 112.38, 115.78, 116.79, 118.37, 123.03, 126.42, 127.23, 128.18, 128.82, 129.97, 136.43, 137.06, 139.03, 148.68, 156.95, 158.81. HRMS: Cald. for C$_{32}$H$_{33}$NO$_3$ (M$^+$) 479.24604, Found: 479.24690.

Entries 5 and 8:

(4) 4-ethenyl-N,N-bis($^4$-methoxyphenyl)benzenamine (Entry 5 only)

$^1$H NMR (300 MHz, CDCl$_3$): δ 3.76 (s, 6H), 5.05-5.09 (dd, $J_1$=0.72 Hz, $J_2$=10.86 Hz, 1H), 5.53-5.59 (dd, $J_1$=0.84 Hz, $J_2$=17.58 Hz, 1H) 6.56-6.65 (dd, $J_1$=10.86 Hz, $J_2$=17.58 Hz, 1H), 6.77-6.89 (m, 6H), 7.00-7.05 (m, 4H), 7.19-7.22 (d, J=8.67 Hz, 2H). $^{13}$C NMR (75 MHz, CDCl$_3$): δ 55.62, 111.25, 114.83, 120.62, 126.69, 127.04, 130.10, 136.49, 140.99, 148.58, 156.00. HRMS Cald. for C$_{22}$H$_{21}$NO$_2$ (M$^+$) 331.15723, Found: 331.15772.

(5) N,N-bis(4-methoxyphenyl)-4-[2-(4-methoxyphenyl)ethenyl]benzenamine $^1$H NMR (300 MHz, CDCl$_3$): δ 3.77 (s, 6H), 3.79 (s, 3H), 6.80-6.91 (m, 10H), 7.03-7.06 (m, 4H), 7.27 (d, J=8.76 Hz, 2H), 7.38 (d, J=8.76 Hz, 2H). $^{13}$C NMR (75 MHz, CDCl$_3$): δ 55.47, 55.64, 114.25, 114.84, 120.88, 125.84, 126.49, 126.66, 127.09, 127.52, 130.18, 130.80, 141.02, 148.11, 155.99, 159.07. mp. 118-120 C. HRMS: Cald. for C$_{29}$H$_{27}$NO$_3$ (M$^+$) 437.19909, Found: 437.19988.

Entries 6 and 7 (Novel Compounds):

(4) 4-ethenyl-N,N-bis(3-methoxyphenyl)benzenamine, R=R$^1$=3OCH$_3$ $^1$H NMR (300 MHz, CDCl$_3$): δ 3.63 (s, 6H), 5.06 (d, J=10.86 Hz, 1H), 5.53 (d, J=17.61 Hz, 1H), 6.48-6.57 (m, 7H), 6.94 (d, J=8.55 Hz, 2H), 7.04 (t, J=8.04 Hz, 2H), 7.17 (m, 2H). $^{13}$C NMR (75 MHz, CDCl$_3$): δ 55.22, 108.42, 110.14, 112.24, 116.86, 124.04, 126.99, 129.77, 132.09, 136.19, 147.16, 148.67, 160.40. HRMS: Cald. for C$_{22}$H$_{21}$NO$_2$ (M$^+$) 331.15723, Found: 331.15790.

(5) N,N-bis(3-methoxyphenyl)-4-[2-(3-methoxyphenyl)ethenyl]benzenamine, R=R$^1$=R$^2$3-OCH$_3$ $^1$H NMR (300 MHz, CDCl$_3$): δ 3.70 (s, 6H), 3.82 (s, 3H), 6.56-6.59 (m, 2H), 6.65-6.70 (m, 4H), 6.77-6.80 (m, 1H), 6.98-7.17 (m, 8H), 7.22-7.24 (t, J=7.95 Hz, 1H), 7.36-7.38

(d, J=8.55 Hz, 2H). $^{13}$C NMR (75 MHz, CDCl$_3$): δ 55.22, 108.54, 110.24, 111.49, 112.93, 116.95, 119.01, 123.96, 126.99, 127.32, 128.42, 129.55, 129.80, 131.58, 139.01, 147.08, 148.59, 159.83, 160.41. HRMS: Cald. for C$_{29}$H$_{27}$NO$_3$ (M$^+$) 437.19909, Found: 437.19988.

EXAMPLE 3

General Procedure for the One Pot Synthesis of Unsymmetrically Substituted diarylaminostilbenes (6) According to Scheme 2

An oven dried Schlenk tube equipped with a magnetic stirring bar was charged with Pd$_2$dba$_3$ (2 mol %) and NaO-t-Bu (3.5 mmol). The tube was capped with a rubber septum, evacuated and then flushed with argon three times. P(isoBuNCH$_2$CH$_2$)$_3$N (4 mol %), 4-aminostyrene (1 mmol), bromobenzene (314 mg, 2 mmol) and toluene (10 mL) were successively added via syringe. After the tube was heated at 60° C. for 3 h, all the starting material was converted in to the N,N-diphenylaminostyrene as judged by TLC. To this reaction mixture, 4-bromotoluene (205 mg, 1.2 mmol) was added and the temperature was raised to 110° C. After heating for another 16 h, the reaction mixture was cooled to room temperature. The reaction mixture was filtered through a celite pad to remove the solid impurities and the filtrate was concentrated in vacuo. The crude product was purified by column chromatography using 1% EtOAc/hexane as eluants to afford the coupled product (6), namely N,N-diphenyl-4-[2-(4-methylphenyl) ethenyl]benzenamine (312 mg, 86%) as a yellow solid (See Entry 1 of Table 3).

Following the above procedure, Pd$_2$dba$_3$ (18.3 mg, 2 mol %), NaO-t-Bu (336 mg, 3.5 mmol), P(isoBuNCH$_2$CH$_2$)$_3$N (13.6 mg, 4 mol %), 4-aminostyrene (119 mg, 1 mmol, 4-bromoanisole (374 mg, 2 mmol), and 10 mL of dry toluene was heated at 60° C. for 3 h and to the same reaction mixture bromobenzene (188 mg, 1.2 mmol) was added and heated at 110° C. for 16 h produced the coupled product 6, namely, N,N-bis(4-methoxyphenyl)-4-[2-phenylethenyl]benzenamine (245 mg, 60%) as a yellow solid after chromatography with 5% EtOAc/hexane mixture. (See Entry 2 of Table 3).

The compounds produced according to the reactions shown in Entries 3-9 of Table 3 were made according to similar methods described above. The coupled products produced include N,N-bis(4-methylphenyl)-4-[2-phenylethenyl]benzenamine (Entries 3 and 5); N,N-bis(3-methylphenyl)-4-[2-phenylethenyl]benzenamine (Entry 4); novel compound N,N-bis(3-methoxyphenyl)-4-[2-phenylethenyl]benzenamine (Entry 6); N,N-bis(4-methoxyphenyl)-4-[2-(4-methylphenyl)ethenyl]benzenamine (Entry 7); N,N-bis(4-methylphenyl)-4-[2-(3-methoxyphenyl)ethenyl]benzenamine (Entry 8) and novel compound N,N-bis(4-methoxyphenyl)-4-[2-(3-methylphenyl)ethenyl]benzenamine (Entry 9).

Results

TABLE 3

One pot synthesis results of unsymmetrically substituted diarylaminostilbenes (6) according to Scheme 2

| Entry | Arylhalide (I) | Aryl halide (II) | T$_1$° C. | T$_2$° C. | Yield % |
|---|---|---|---|---|---|
| 1 | Ph—Br | 4-Me-C$_6$H$_4$—Br | 60 | 110 | 86 |
| 2 | MeO—C$_6$H$_4$—Br | Ph—Br | 60 | 110 | 60 |
| 3 | 4-Me-C$_6$H$_4$—I | Ph—I | 60 | 110 | 81 |
| 4 | 3-Me-C$_6$H$_4$—Br | Ph—I | 85 | 110 | 83 |
| 5 | 4-Me-C$_6$H$_4$—Br | Ph—Br | 85 | 110 | 91 |
| 6 | 3-MeO-C$_6$H$_4$—Br | Ph—Br | 85 | 110 | 75* |

TABLE 3-continued

One pot synthesis results of unsymmetrically substituted diarylaminostilbenes (6) according to Scheme 2

| Entry | Arylhalide (I) | Aryl halide(II) | $T_1°$ C. | $T_2°$ C. | Yield % |
|---|---|---|---|---|---|
| 7 | MeO–〈Ph〉–Br | 〈Ph〉–Br | 60 | 110 | 44 |
| 8 | CH₃–〈Ph〉–Br | 〈Ph(MeO)〉–Br | 85 | 110 | 46 |
| 9 | MeO–〈Ph〉–Br | 〈Ph(CH₃)〉–Br | 60 | 110 | 43* |

*novel compounds

Spectral Data for Table 3
Entry 1:

(6) N,N-diphenyl-4-[2-(4-methylphenyl)ethenyl]benzenamine $^1$H NMR (300 MHz, CDCl$_3$): δ 3.34 (s, 3H), 7.97-8.15 (m, 12H), 8.21-8.26 (m, 4H), 8.34-8.39 (m, 4H). $^{13}$C NMR (75 MHz, CDCl$_3$): δ 21.22, 122.90, 123.69, 124.36, 126.19, 126.99, 127.13, 127.19, 129.23, 129.34, 131.74, 134.78, 137.11, 147.10, 147.54. mp. 162-164° C. HRMS: Cald. for C$_{27}$H$_{23}$N (M$^+$) 361.18305, Found: 361.18340.

Entry 2:

(6) N,N-bis(4-methoxyphenyl)-4-[2-phenylethenyl]benzenamine $^1$H NMR (300 MHz, CDCl$_3$): δ 3.77 (s, 6H), 6.80-6.83 (m, 4H), 6.88-6.95 (m, 3H), 7.00-7.06 (m, 5H), 7.21 (d, J=6Hz, 1H), 7.29-7.32 (m, 4H), 7.44-7.47 (m, 2H). $^{13}$C NMR (75 MHz, CDCl$_3$): δ 55.42, 114.63, 120.40, 125.95, 126.13, 126.56, 126.99, 128.29, 128.57, 129.47, 137.75, 140.67, 148.24, 155.85. mp. 120-122° C. Cald. for C$_{28}$H$_{25}$NO$_2$ (M$^+$) 407.18853, Found: 407.18925.

Entry 6 (Novel Compound):

(6) N,N-bis(3-methoxyphenyl)-4-[2-phenylethenyl]benzenamine (R=R$^1$=3-OCH$_3$, R$^2$=H)

Entry 9 (Novel Compound):

(6) N,N-bis(4-methoxyphenyl)-4-[2-(3-methylphenyl)ethenyl]benzenamine (R=R$^1$=4=OCH$_3$, R$^2$=3-CH$_3$)

Entries 3-9:

It is expected that spectra data generated according to the methods described herein will confirm the structure of the compounds listed herein.

EXAMPLE 4

The general procedure for the one pot synthesis of unsymmetrically substituted diarylaminostilbene derivatives (6) described in Example 3 was followed except that the amounts of aryl halides used were altered.

Following the above procedure, Pd$_2$dba$_3$ (18.3 mg, 2 mol %), NaO-t-Bu (336 mg, 3.5 mmol), P(isoBuNCH$_2$CH$_2$)$_3$N (13.6 mg, 4 mol %), 4-aminostyrene (119 mg, 1 mmol), 4-iodotoluene (218 mg, 1 mmol), and 10 mL of dry toluene was heated at 60° C. for 3 h and to the same reaction mixture iodobenzene (449 mg, 2.2 mmol) was added and heated at 110° C. for 16 h produced the coupled product 7, namely, N-(4-methylphenyl)-N-(Phenyl)-4-[2-phenylethenyl]benzenamine (282 mg, 78%) as a yellow solid after chromatography with 1% EtOAc/hexane mixture. (See Entry 1 of Table 4).

Following the above procedure, Pd$_2$dba$_3$ (18.3 mg, 2 mol %), NaO-t-Bu (336 mg, 3.5 mmol), P(isoBuNCH$_2$CH$_2$)$_3$N (13.6 mg, 4 mol %), 4-aminostyrene (119 mg, 1 mmol), 4-iodoanisole (234 mg, 1 mmol), and 10 mL of dry toluene was heated at 60° C. for 3 h and to the same reaction mixture iodobenzene (449 mg, 2.2 mmol) was added and heated at 110° C. for 16 h produced the coupled product 7, namely, N-(4-methoxyphenyl)-N-(Phenyl)-4-[2-phenylethenyl]benzenamine (299 mg, 79%) as a viscous yellow liquid after chromatography with 1-2% EtOAc/hexane mixture. (See Entry 2 of Table 4).

The compounds produced according to the reactions shown in Entries 3 and 4 of Table 4 were made according to methods analogous to those described above but with the components as shown. The coupled products produced include N-(4-methylphenyl)-N-(Phenyl)-4-[2-phenylethenyl]benzenamine for Entry 3 (Same as Entry 1) and N-(4-methoxyphenyl)-N-(Phenyl)-4-[2-phenylethenyl]benzenamine for Entry 4 (Same as Entry 2).

Results

TABLE 4

One pot synthesis results of unsymmetrically substituted diarylaminostilbenes (6) according to Scheme 3

| Entry | Arylhalide (I) | Time in hrs | $T_1$ °C. | Aryl halide(II) | $T_2$ °C. | Time in hrs | Yield |
|---|---|---|---|---|---|---|---|
| 1 | 4-methylphenyl-I | 3 | 60 | phenyl-I | 110 | 16 | 78 |
| 2 | 4-methoxyphenyl-I | 3 | 60 | phenyl-I | 110 | 16 | 79 |
| 3 | 4-methylphenyl-Cl | 12 | 110 | phenyl-I | 110 | 16 | 76 |
| 4 | 4-methoxyphenyl-Cl | 12 | 110 | phenyl-I | 110 | 16 | 71 |

Spectral Data for Table 4
Entries 1 and 3:

(7) N-4-methylphenyl)-N-(Phenyl)-4-[2-phenylethenyl]benzenamine $^1$H NMR (300 MHz, CDCl$_3$): δ 2.31 (s, 3H), 6.99-7.09 (m, 11H), 7.20-7.22 (m, 3H), 7.29-7.36 (m, 4H), 7.46 (d, J=7.32 Hz, 2H). $^{13}$C NMR (75 MHz, CDCl$_3$): δ 21.07, 122.82, 123.21, 124.20, 125.34, 126.47, 126.98, 127.40, 127.49, 128.42, 128.82, 129.38, 130.19, 131.26, 133.24, 137.86, 145.13, 147.73, 147.88. mp. 134-136° C. HRMS: Cald. for C$_{27}$H$_{23}$N (M$^+$) 361.18305, Found: 361.18537.

Entries 2 and 4:

(7) N-(4-methoxyphenyl)-N-(Phenyl)-4-[2-phenylethenyl]benzenamine $^1$H NMR (300 MHz, CDCl$_3$): δ 3.80 (s, 3H), 6.83-6.86 (m, 2H), 6.97-7.10 (m, 9H), 7.20-7.25 (m, 3H), 7.31-7.37 (m, 4H), 7.46-7.49 (m, 2H). $^{13}$C NMR (75 MHz, CDCl$_3$): δ 55.70, 114.97, 122.47, 123.54, 126.44, 126.77, 127.37, 127.44, 127.61, 128.41, 128.83, 129.34, 130.84, 137.87, 140.59, 147.86, 147.95, 156.48. HRMS: Cald. for C$_{27}$H$_{23}$NO (M$^+$) 377.17796, Found: 377.17850.

EXAMPLE 5

The procedure for the one pot synthesis of symmetrically substituted diarylaminostyrenes was performed according to the general procedure given in Example 1 for producing diarylaminostyrenes except that only 2.2 equivalents of aryl halide was used with the conditions given in Scheme 4 shown above. In this instance, only a double amination reaction was performed at temperatures ranging from 60 to 110° C.

Results

TABLE 5

One pot synthesis results of symmetrically substituted diarylaminostyrenes (4) according to Scheme 4

| Entry | Arylhalide | Temp (T° C.) | Time in hrs | Yield % |
|---|---|---|---|---|
| 1 | phenyl-Br | 60 | 3 | 90 |
| 2 | 4-methylphenyl-Br | 85 | 3 | 86 |
| 3 | 3-methylphenyl-Br | 85 | 3 | 86 |
| 4 | 3,5-dimethylphenyl-Br | 85 | 3 | 81* |
| 5 | 4-tert-butylphenyl-Br | 85 | 3 | 91* |

TABLE 5-continued

One pot synthesis results of symmetrically substituted diarylaminostyrenes (4) according to Scheme 4

| Entry | Arylhalide | Temp (T° C.) | Time in hrs | Yield % |
|---|---|---|---|---|
| 6 | Cl—⟨phenyl⟩—Br | 85 | 3 | 78* |
| 7 | ⟨naphthyl⟩—Br | 100 | 12 | 90 |
| 8 | CH₃—⟨phenyl⟩—Cl | 110 | 16 | 78 |

*novel compounds

The coupled products produced include 4-ethenyl-N,N-diphenylbenzenamine (Entry 1); 4-ethenyl-N,N-bis(4-methylphenyl)benzenamine (Entries 2 and 8); 4-ethenyl-N,N-bis(3- methylphenyl)benzenamine (Entry 3); novel compound 4-ethenyl-N,N-bis(3,5-dimethylphenyl)benzenamine, R=R$^1$=3,5-dimethyl (Entry 4); novel compound 4-ethenyl-N,N-bis(4-ter-butylphenyl)benzenamine, R=R$^1$=4-ter-butyl (Entry 5); novel compound 4-ethenyl-N,N-bis(4-chlorophenyl)benzenamine, R=R$^1$=4-Cl (Entry 6) and 4-ethenyl-N,N-bis(Naphthyl)benzenamine (Entry 7).

It is expected that spectral data generated according to the methods described herein will confirm the structure of the compounds listed herein.

EXAMPLE 6

The general procedure for the one pot double amination of unsymmetrically substituted diarylaminostyrenes (4) as described in Example 1 was followed except that 1 equivalent of aryl bromide and 1.1 equivalent of aryl chloride was used. Furthermore, the amination of the arylbromide and aryl chloride was carried out by raising the temperature from 60 to 110° C. over a period of three (3) hours and continuing heating at 110° C. for an additional 13 hours. (No subsequent arylation step was performed.) Results are shown in Table 5 below.

Results

TABLE 6

One pot synthesis results of unsymmetrically substituted diarylaminostyrenes (4) according to Scheme 5

| Entry | Arylhalide (I) | Aryl halide(II) | Yield |
|---|---|---|---|
| 1 | MeO—⟨phenyl⟩—Br | ⟨phenyl⟩—Cl | 68* |
| 2 | CH₃—⟨phenyl⟩—Br | ⟨phenyl⟩—Cl | 81* |
| 3 | MeO—⟨phenyl⟩—Br (meta) | ⟨phenyl⟩—Cl | 86* |

*novel compounds

The coupled products produced include novel compound 4-ethenyl-N-(4-methoxyphenyl)-N-(4-methylPhenyl)benzenamine, R=4-OCH$_3$, R$^1$=4-CH$_3$(Entry 1); novel compound 4-ethenyl-N-(3-methylphenyl)-N-(4-methylPhenyl)benzenamine, R=3-CH$_3$, R$^1$=4-CH$_3$ (Entry 2) and novel compound 4-ethenyl-N-(3-methoxyphenyl)-N-(4-methylphenyl)benzenamine, R=3-OCH$_3$, R$^1$=4-CH$_3$ (Entry 3).

CONCLUSION

The present invention provides an efficient, economical and environmentally friendly method for producing a variety of compounds, including novel compounds, such as novel styrenes and novel stilbenes, using sequential reactions in a single pot with the same catalyst system. Not only is less material being used to produce the final product, unlike known sequenced reactions, the same catalyst system can be used for a complete set of sequential reactions.

The resulting yield is, in most embodiments, at least comparable or better than yields of known reaction methods requiring at least two pots and multiple catalysts. Yields of at least about 80% up to 98% have been observed, although it is possible even higher yields can be obtained under varying reaction conditions. In other embodiments, the yields may be lower, although novel products have been produced.

Embodiments of the invention comprise novel one pot methodologies for the synthesis of various complex molecules, including N,N-diarylaminostilbenes and N,N-diarylaminostyrenes. Synthesis of such molecules has previously required time-consuming, expensive multistep reactions requiring more than one pot and/or multiple catalysts or catalyst systems. Embodiments of the invention have the additional advantage of being able to use the same catalyst system for each set of reactions, such as a double amination reaction and an intermolecular Heck coupling, thus reducing costs and further increasing efficiency. (As used herein, each reaction can have one or more couplings).This type of strategy has significant potential for the design and synthesis of many complex molecules in which both the C—N and C—C bonded moieties are fundamental features. Additionally, in most embodiments, the catalyst loading is at least comparable to known multi-pot/multi-catalyst reactions.

Many of the resulting compounds described herein are useful as electro photographic photoconductors and photoreceptors. Many of the compounds are also known to exhibit an amino conjugation effect in their fluorescence enhancement spectra. Other possible uses include use as a new ionophore for transition metals among several other applications. It is likely that many, if not all, of the novel compounds produced according to the novel methods described herein have the same or similar properties.

All publications, patents, and patent documents cited in the specification are incorporated by reference herein, each in their entirety, as though individually incorporated by reference. In the case of any inconsistencies, the present disclosure, including any definitions therein, will prevail.

Although the present invention has been described in considerable detail with reference to certain preferred versions thereof, other versions are possible. For example, it is possible that other sequenced reactions of C—N and C—C bonded moieties may be performed using the methods described herein. Such methods include, but are not limited to, Suzuki-Heck reactions, Buchwald-Hartwig-Heck reactions, Suzuki reactions followed an amination reaction, and so forth. It is also possible that more than three couplings may be performed in one pot using the methods described herein. Therefore, the spirit and scope of the appended claims should not be limited to the description of the preferred embodiments contained herein.

What is claimed is:

1. A method for producing sequenced intermediate and final reaction products comprising: performing, in one pot, a first reaction at a lower temperature to produce an intermediate styrene reaction product followed by a second reaction at a higher temperature to produce the final stilbene reaction product, wherein the first and second reactions are performed in the presence of a homogenous catalyst system comprising a proazaphosphatrane in combination with a palladium compound.

2. The method of claim 1 wherein the lower temperature is about 40 to 60° C. and the higher temperature is about 100 to 120° C.

3. The method of claim 1 wherein the first reaction is a double amination and the second reaction is an arylation.

4. The method of claim 3 wherein the double amination comprises a first Buchwald-Hartwig amination and a second Buchwald-Hartwig amination, and the arylation is an intermolecular Heck arylation.

5. The method of claim 4 wherein a first aryl halide is used in the first Buchwald-Hartwig reaction and a second aryl halide is used in the Buchwald-Hartwig second reaction.

6. The method of claim 1 wherein the homogenous catalyst has a formula of:

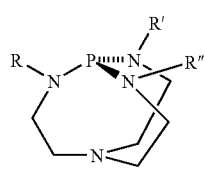

wherein R', R" and R'" are selected from the group consisting of H, $(C_1$-$C_8)$alkyl, and $(C_6$-$C_9)$aryl.

7. The method of claim 6 where $R=R^1=R^2$=isobutyl and the palladium compound is $Pd_2(dba)_3$.

8. The method of claim 1 wherein the styrene is 4-aminostyrene.

9. The method of claim 1 wherein the stilbene is N,N-diarylaminostilbene.

10. The method of claim 9 wherein the N,N-diarylaminostilbene comprises:

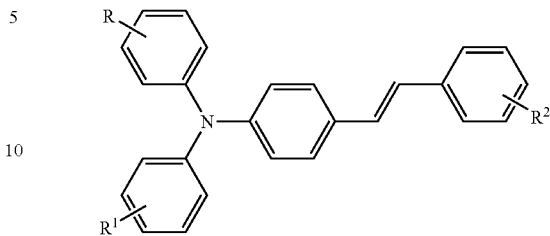

wherein each R, $R^1$ and $R^2$ can individually be H, one or more $(C_1$-$C_8)$alkyl, one or more $(C_6$-$C_9)$aryl or one or more $(C_1$-$C_8)$alkoxy.

11. The method of claim 10 wherein $R=R^1$=H, 4-$CH_3$, 3-$CH_3$, 3-$OCH_3$ or 4-$OCH_3$ and $R^2$=4-$CH_3$, 3-$CH_3$, 3-$OCH_3$, 4-$OCH_3$ or 3,5-dimethyl.

12. The method of claim 10 wherein $R=R^1=R^2$=H, 4-$CH_3$, 3-$CH_3$, 2-$CR_3$, 3-$OCH_3$, 4-$OCH_3$, 4-Cl, 4-tert-butyl or 3,5-dimethyl.

13. The method of claim 10 wherein $R^1=R^2$=H, 4-$CH_3$, 3-$CH_3$ or Cl and R=4-$CH_3$, 4-$OCH_3$, 3-$OCH_3$, 4-tert-butyl or 3-$CH_3$.

14. The method of claim 10 wherein R, $R^1$ and $R^2$=3,5-dimethyl, 3-$CH_3$, 3-$CH_3$-4-$OCH_3$ or 3-$OCH_3$ or $R=R^1$=3-$OCH_3$ and $R^2$=H, or $R=R^1$=4-$OCH_3$ and $R^2$=3-$CH_3$.

15. The method of claim 9 wherein the N,N-diarylaminostilbene is trans-4-N,N-diarylaminostilbene.

16. The method of claim 15 wherein the trans-4-N,N-diarylaminostilbene is symmetrically substituted.

17. The method of claim 15 wherein the trans-4-N,N-diarylaminostilbene is unsymmetrically substituted.

18. A stilbene compound made according to the method of claim 1, wherein the stilbene compound is the final reaction product comprising:

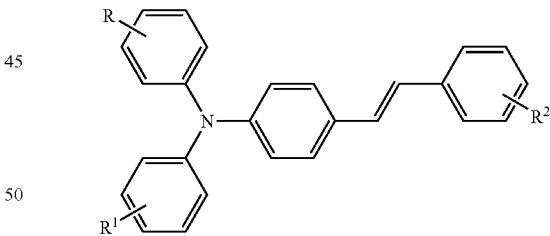

wherein R, $R^1$ and $R^2$=3,5-dimethyl, 3-$CH_3$, 3-$CH_3$-4-$OCH_3$ or 3-$OCH_3$, or $R=R^1$=3-$OCH_3$ and $R^2$=H; or $R=R^2$=4-$OCH_3$ and $R^2$=3-$CH_3$.

19. The stilbene compound of claim 18 comprising a trans-4-N,N-diarylaminostilbene selected from the group consisting of N,N-bis(3,5-dimethylphenyl)-4-[2-(3,5-dimethylphenyl)ethenyl]benzenamine, N,N-bis(3-methyl-4-methoxyphenyl)-4-[2-(3-methyl-4-methoxyphenyl) ethenyl]benzenamine, N,N-bis(3-methoxyphenyl)-4-[2-(3-methoxyphenyl)ethenyl]benzenamine, N,N-bis(3-methoxyphenyl)-4-[2-phenylethenyl]benzenamine, N,N-bis(4-methoxyphenyl)-4-[2-(3-methylphenyl)ethenyl] benzenamine and N,N-bis(3-methylphenyl)-4-[2-(3-dimethylphenyl)ethenyl]benzenamine.

20. A styrene compound made according to the method of claim 1, wherein the styrene compound is the intermediate reaction product comprising:

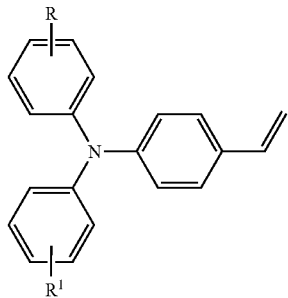

wherein $R=R^1=$3,5-dimethyl, $3CH_3$, 3-$CH_3$-4-$OCH_3$, 4-tert-butyl or 4-Cl, or $R^1$=4-$CH_3$ and R=4-$OCH_3$ or $3CH_3$, or $R^1$=3-$OCH_3$ and R =4$CH_3$.

21. The styrene compound of claim 20 comprising a N,N-diarylaminostyrene selected from the group consisting of 4-ethenyl-N,N-bis(3,5-dimethylphenyl)benzenamine, 4-ethenyl-N,N-bis(3-methyl-4-methoxyphenyl)benzenamine, 4-4-ethenyl-N,N-bis(4-tert-butylphenyl)benzenamine, 4-ethenyl-N,N-bis(4-chlorophenyl)benzenamine, 4-ethenyl-N-(4-methoxyphenyl)-N-(4-methylPhenyl)benzenamine, 4-ethenyl-N-(3-methylphenyl)-N-(4-methylPhenyl)benzenamine, 4-ethenyl-N-(3-methoxyphenyl)-N-(4-methylPhenyl)benzenamine and 4-ethenyl-N,N-bis(3-methylphenyl)benzenamine.

* * * * *

UNITED STATES PATENT AND TRADEMARK OFFICE
CERTIFICATE OF CORRECTION

PATENT NO.       : 7,276,627 B2
APPLICATION NO. : 11/099415
DATED            : October 2, 2007
INVENTOR(S)      : Valsan et al.

It is certified that error appears in the above-identified patent and that said Letters Patent is hereby corrected as shown below:

On the title page, item (56), under "Other Publications", in column 2, line 30, after "7" delete "." and insert -- , --, therefor.

On the title page, item (56), under "Other Publications", in column 2, line 35, delete "Organopalldium" and insert -- Organopalladium --, therefor.

On the title page, item (56), under "Other Publications", in column 2, line 40, delete "Starbust" and insert -- Starburst --, therefor.

On page 2, item (56), under "Other Publications", in column 1, line 15, delete "Macromolecules" and insert -- Macromolecular --, therefor.

On page 2, item (56), under "Other Publications", in column 2, line 13, delete "trans4" and insert -- trans-4 --, therefor.

On page 2, item (56), under "Other Publications", in column 2, line 19, delete "Letters4(5)" and insert -- Letters, 4(5) --, therefor.

On page 2, item (56), under "Other Publications", in column 2, line 29, before "Oct." insert -- ( --.

In column 3, line 42, delete "$R_1$" and insert -- $R^1$ --, therefor.

In column 7, line 65, delete "(3)hrs" and insert -- (3) hrs --, therefor.

In column 9, line 27, delete "$Pd_{2(dba)3}$" and insert -- $Pd_2(dba)_3$ --, therefor.

In column 14, line 24, delete "$4-CH_33-CH_3$" and insert -- $4-CH_3$, $3-CH_3$ --, therefor.

In column 14, line 24, delete "$_3-OCH_3$" and insert -- $3-OCH_3$ --, therefor.

In column 15, line 15, delete "$R_1$" and insert -- $R^1$ --, therefor.

In column 15, line 23, delete ";a" and insert -- ; a --, therefor.

In column 15, line 36, after "benzenamine" insert -- , --.

In column 16, line 3, delete "methylPhenyl" and insert -- methylphenyl --, therefor.

In column 16, line 4, delete "methylPhenyl" and insert -- methylphenyl --, therefor.

UNITED STATES PATENT AND TRADEMARK OFFICE
CERTIFICATE OF CORRECTION

PATENT NO. : 7,276,627 B2
APPLICATION NO. : 11/099415
DATED : October 2, 2007
INVENTOR(S) : Valsan et al.

It is certified that error appears in the above-identified patent and that said Letters Patent is hereby corrected as shown below:

In column 16, line 5, delete "methylPhenyl" and insert -- methylphenyl --, therefor.

In column 22, line 9, delete "δ55.56" and insert -- δ 55.56 --, therefor.

In column 22, line 28, delete "($^4$-methoxyphenyl)" and insert -- (4-methoxyphenyl) --, therefor.

In column 22, line 48, delete "120 C." and insert -- 120° C. --, therefor.

In column 22, line 52, delete "3OCH$_3$" and insert -- 3-OCH$_3$ --, therefor.

In column 22, line 63, delete "R$^2$3-OCH$_3$" and insert -- R$^2$=3-OCH$_3$ --, therefor.

In column 24, line 5, delete "1 mmol," and insert -- 1 mmol), --, therefor.

In column 25, line 50, after "126.99" insert -- 127.16 --.

In column 25, line 51, after "122° C." insert -- HRMS: --.

In column 25, line 61, delete "4=OCH$_3$" and insert -- 4-OCH$_3$ --, therefor.

In column 27, line 35, delete "N-4" and insert -- N-(4 --, therefor.

In column 30, line 21, delete "methylPhenyl" and insert -- methylphenyl --, therefor.

In column 30, line 23, delete "methylPhenyl" and insert -- methylphenyl --, therefor.

In column 32, line 23, in Claim 12, delete "2-CR$_3$" and insert -- 2-CH$_3$ --, therefor.

In column 32, line 23, in Claim 12, delete "$_4$-Cl" and insert -- 4-Cl --, therefor.

In column 32, line 29, in Claim 14, after "3-OCH$_3$" insert -- , --.

In column 32, line 29, in Claim 14, delete "R$_1$" and insert -- R$^1$ --, therefor.

In column 32, line 55, in Claim 18, delete "3-OCH$_3$," and insert -- 3-OCH$_3$; --, therefor.

In column 32, line 55, in Claim 18, delete "R$_2$" and insert -- R$^1$ --, therefor.

UNITED STATES PATENT AND TRADEMARK OFFICE
CERTIFICATE OF CORRECTION

PATENT NO. : 7,276,627 B2
APPLICATION NO. : 11/099415
DATED : October 2, 2007
INVENTOR(S) : Valsan et al.

It is certified that error appears in the above-identified patent and that said Letters Patent is hereby corrected as shown below:

In column 34, line 10, in Claim 21, delete "methylPhenyl" and insert -- methylphenyl --, therefor.

In column 34, line 11, in Claim 21, delete "methylPhenyl" and insert -- methylphenyl --, therefor.

In column 34, lines 12-13, in Claim 21, delete "methylPhenyl" and insert -- methylphenyl --, therefor.

Signed and Sealed this

Eighteenth Day of December, 2007

JON W. DUDAS
*Director of the United States Patent and Trademark Office*